United States Patent
Koester et al.

(10) Patent No.: US 11,008,282 B2
(45) Date of Patent: May 18, 2021

(54) BICYCLIC-COMPOUNDS FOR USE AS A MEDICAMENT, IN PARTICULAR FOR TREATMENT OF PARKINSON'S DISEASE

(71) Applicants: Hubert Koester, Morcote (CH); CAPROTEC BIOANALYTICS GMBH, Berlin (DE)

(72) Inventors: Hubert Koester, Morcote (CH); Lisa Von Kleist, Berlin (DE); Simon Michaelis, Berlin (DE); Kathrin Bartho, Dreieich (DE); Marén Schlief, Berlin (DE); Mathias Dreger, Berlin (DE); Anna K. Schrey, Berlin (DE); Michael Sefkow, Berlin (DE); Friedrich Kroll, Duelmen (DE); Daniel Ohlendorf, Berlin (DE); Yan Luo, Berlin (DE)

( * ) Notice: Subject to any disclaimer, the term of this patent is extended or adjusted under 35 U.S.C. 154(b) by 0 days.

(21) Appl. No.: 16/063,297

(22) PCT Filed: Dec. 19, 2016

(86) PCT No.: PCT/EP2016/081792
§ 371 (c)(1),
(2) Date: Jun. 18, 2018

(87) PCT Pub. No.: WO2017/103278
PCT Pub. Date: Jun. 22, 2017

(65) Prior Publication Data
US 2018/0370906 A1 Dec. 27, 2018

(30) Foreign Application Priority Data

Dec. 18, 2015 (EP) .................................... 15201180
Jun. 15, 2016 (EP) .................................... 16174650

(51) Int. Cl.
| | | |
|---|---|---|
| *C07C 233/58* | (2006.01) |
| *C07C 35/36* | (2006.01) |
| *C07C 205/05* | (2006.01) |
| *C07C 205/18* | (2006.01) |
| *A61K 31/047* | (2006.01) |
| *A61K 31/045* | (2006.01) |
| *A61K 31/04* | (2006.01) |
| *A61K 31/166* | (2006.01) |
| *A61P 3/04* | (2006.01) |
| *A61P 25/28* | (2006.01) |
| *A61P 25/16* | (2006.01) |
| *A61P 31/06* | (2006.01) |
| *C07C 237/10* | (2006.01) |
| *C07C 271/20* | (2006.01) |
| *C07C 271/22* | (2006.01) |
| *C07C 235/66* | (2006.01) |
| *C07C 235/74* | (2006.01) |
| *C07C 231/02* | (2006.01) |

(52) U.S. Cl.
CPC .............. *C07C 237/10* (2013.01); *A61P 3/04* (2018.01); *A61P 25/16* (2018.01); *A61P 25/28* (2018.01); *A61P 31/06* (2018.01); *C07C 231/02* (2013.01); *C07C 235/66* (2013.01); *C07C 235/74* (2013.01); *C07C 271/20* (2013.01); *C07C 271/22* (2013.01); *C07C 2601/14* (2017.05); *C07C 2602/10* (2017.05)

(58) Field of Classification Search
CPC ..... C07C 233/58; C07C 35/36; C07C 205/05; C07C 205/18; A61K 31/047; A61K 31/045; A61K 31/04; A61K 31/166; A61P 3/04; A61P 25/28; A61P 25/16; A61P 31/06
USPC .................. 514/619; 564/156, 180, 166, 170
See application file for complete search history.

(56) References Cited

U.S. PATENT DOCUMENTS

| | | | |
|---|---|---|---|
| 4,937,371 A | 6/1990 | Carson et al. |
| 2004/0034011 A1 | 2/2004 | Backstrom et al. |

FOREIGN PATENT DOCUMENTS

| | | |
|---|---|---|
| EP | 2018844 | 1/2009 |
| JP | 63115834 | 5/1988 |

(Continued)

OTHER PUBLICATIONS

Von Kleist, L., S. Michaelis, K. Bartho, O. Graebner, M. Schlief, M. Dreger, A. Schrey, M. Sefkow, F. Kroll, H. Koester and Y. Luo, "Ident. of Poten. Off-target Toxic. Liab. of Catechol-O-methyltransferase Inhibit. by Diff. Competition Capture Compound Mass Spectrometry" (2016), 59: pp. 4664-4675. (Year: 2016).*

(Continued)

*Primary Examiner* — Joseph R Kosack
*Assistant Examiner* — Sagar Patel
(74) *Attorney, Agent, or Firm* — JMB Davis Ben-David

(57) ABSTRACT

The invention relates to novel small molecule compounds having a basic structure as depicted by formula (A), where in particular exemplary embodiments $R^1$ is —OH, $R^2$ is —$NO_2$ and $R^3$ is H, $R^4$ and $R^5$ are H, one of $R^6$ and $R^7$ is selected from H, —$CONH_2$, and —$CONR^9_2$, and the other one is selected from —$CONR^9_2$ and —$CONR^{11}R^9$, wherein $R^9$ and $R^{11}$ are (possibly multiply) substituted alkyl and H or alkyl, respectively. The compounds of the invention inhibit the enzyme Catechol-O-methyltransferase (COMT) and exhibit a low off-target profile. The compounds are provided for use as a medicament, in particular for use in prevention or treatment of Parkinson's disease.

15 Claims, 10 Drawing Sheets

(56) References Cited

FOREIGN PATENT DOCUMENTS

| JP | 2264743 | 10/1990 | | |
|---|---|---|---|---|
| JP | 4154736 | 5/1992 | | |
| WO | 02/22551 | 3/2002 | | |
| WO | WO-0222551 A1 * | 3/2002 | ............ | C07C 45/00 |
| WO | 2015191640 | 10/2016 | | |

OTHER PUBLICATIONS

Harold R. W. Ansink Et Al.: "Aromatic sulfonation. Part 120. Reaction of dihydroxy- and dimesyloxy-naphthalenes with sulfur trioxide in nitromethane. Directing effects and influence of initial sulfation on the product distributions", Journal of the Chemial Society, Perkin Transations 2: Physical Organic Chemistry, vol. 2, No. 4, Jan. 1, 1993, p. 721.

Ansink et al "Aromatic sulfonation. Part 120. Reaction of dihydroxy- and dimesyloxy-naphthalenes with sulfur trioxide in nitromethane. Directing effects and the influence of initial sulfation on the product distributions", Journal of the Chemical Society, Perkin Transactions 2, pp. 721-727.

* cited by examiner tolcapone entacapone

CPT-212

CPT-401 inactive TCP-CC (CPT-220)

active TCP-CC (CPT-224)

| Protein | Uniprot ID | Full name | Assay against C1 | | Assay against C2 | | Assay against C3 | | Assay against C4 | |
|---|---|---|---|---|---|---|---|---|---|---|
| | | | FC | p-value | FC | p-value | FC | p-value | FC | p-value |
| HIBCH | Q6NVY1 | 3-hydroxy-isobutyryl-CoA hydrolase, mitochondrial | 14,2 | 0,0002 | 1,04 | 0,0004 | 1 | 0,001 | 5,35 | 0,002 | tolcapone (CPT-425) and entacapone (CPT-427)

CPT-00352-01-01; [452.48]; 31
98% at 2 µM; 75% at 0.1 µM (B9)

CPT-00351-01-01; [552.60]; 38
99% at 2 µM; 85% at 0.1 µM (B10)

CPT-00385-01-01; [585.63]; 41 (B11)
99% at 2 µM; 84% at 0.1 µM

CPT-00386-01-01; [613.68]; 43
97% at 2 µM; 80% at 0.1 µM

CPT-00350-01-01; [606.69]; 42 (B13)
98% at 2 µM; 74% at 0.1 µM

BICYCLIC-COMPOUNDS FOR USE AS A MEDICAMENT, IN PARTICULAR FOR TREATMENT OF PARKINSON'S DISEASE

CROSS-REFERENCE TO RELATED APPLICATIONS

This is the U.S. National Stage of International Application No. PCT/EP2016/081792 filed Dec. 19, 2016, which was published in English under PCT Article 21(2), and which in turn claims the benefit of European Patent Application Nos. 15201180.5 filed Dec. 18, 2015 and 16174650.8 filed on Jun. 15, 2016.

The present invention relates to novel small molecule compounds for use as a medicament, in particular for use in prevention or treatment of Parkinson's disease.

BACKGROUND OF THE INVENTION

Over the last 50 years, Catechol-O-methyltransferase (COMT), a magnesium dependent enzyme involved in the degradation of neurotransmitters in the brain, has become an attractive target for the treatment of various peripheral and central nervous system disorders. The enzyme exists in two forms; a soluble form (S-COMT) and a membrane bound form (MB-COMT) and is ubiquitously expressed.

Co-administration of a COMT inhibitor with Levodopa (L-DOPA), a precursor of dopamine, and an aromatic amino acid decarboxylase (AADC) inhibitor, increases the half-life of L-DOPA in vivo. Thus, COMT inhibitors are candidates for the adjunctive treatment of Parkinson's disease. Clinically relevant COMT inhibitors are exemplified by nitecapone (OR-462), entacapone (OR-611), tolcapone (Ro 40-7592), nebicapone (BIA3-202), and opicapone (BIA9-1967). The sole clinical application of COMT inhibitors so far is the co-administration with L-DOPA and an AADC inhibitor using entacapone and opicapone which is in Phase III trials. The other inhibitors were discontinued or withdrawn from the market due to either lack of efficiency or safety concerns.

The use of tolcapone, which acts both centrally and peripherally, has caused severe hepatotoxicity in several cases. Entacapone, which acts mainly in the periphery, has a more favorable toxicity profile but suffers from bioavailability issues.

The objective of the present invention is the provision of a novel COMT inhibitor with reduced side-effects (hepatotoxicity) and increased potency. This objective is attained by the subject matter of the independent claims.

Terms and Definitions

As used herein, unless otherwise specified, the term "substituted", when used in the context of a chemical moiety, signifies that one or several hydrogen atoms of the chemical moiety has been replaced by a non-hydrogen substituent atom or substituent moiety selected from -D (deuterium), —F, —Cl, —Br, —I, =O, —OH, —OR, =S, —SH, —OSO$_3$H, —OSO$_3$R, —SO$_3$H, —SO$_2$R, —SO$_2$NH$_2$, —SO$_2$NHR, —SO$_2$NR$_2$, —OPO$_3^{2-}$, —NH$_2$, —NHR, —COOH, —CONH$_2$, —OCOOH, —NHCONH$_2$, —CN, —NC, —CNO, —NCO, —CNS, —SCN, CF$_3$, CHF$_2$, CH$_2$F, wherein R is a C$_1$-C$_8$ alkyl, C$_2$-C$_8$ alkenyl, C$_2$-C$_8$ alkynyl, C$_3$-C$_{10}$ cycloalkyl, 5- to 10-membered aryl or heteroaryl, and a substituent moiety consisting of 2 to 25 atoms selected from C, N, O, S and F, plus any appropriate amount of H atoms, wherein the substituent moiety has a molecular mass of between 29 and 400 g/mol.

As used herein, unless otherwise specified, the term "alkyl" refers to a saturated hydrocarbon substituent group that is linear or branched. Examples of alkyl groups include, without limitation, methyl, ethyl, propyl, n-butyl, isobutyl, pentyl, isopentyl, neopentyl, hexyl, 2-methylpentyl, 3-methylpentyl, 2,2-methylpentyl, 2,3-methylpentyl and the like.

As used herein, unless otherwise specified, the term "alkenyl" refers to an unsaturated hydrocarbon substituent group including at least one carbon-carbon double bond. The alkenyl can be linear or branched.

As used herein, unless otherwise specified, the term "alkynyl" refers to an unsaturated hydrocarbon substituent group including at least one carbon-carbon triple bond. The alkynyl can be linear or branched. One example is the ethynyl (CCH) group.

As used herein, unless otherwise specified, the term "heteroalkyl" refers to a saturated hydrocarbon substituent group, that is linear or branched, wherein at least one carbon is replaced by an oxygen atom, a sulfur atom or a nitrogen atom.

As used herein, unless otherwise specified, the term "cycloalkyl" refers to a saturated cyclic hydrocarbon substituent group.

As used herein, unless otherwise specified, the term "heterocyclic alkyl" refers to a saturated cyclic group wherein at least one carbon is replaced with an oxygen, a nitrogen or a sulphur atom. Examples of saturated heterocycle substituent groups include, without limitation, morpholine, piperazine, pyrrolidine, thiolane, tetrahydrofuran, imidazolidine, pyrazolidine, oxazolidine, thiazolidine, piperidine, oxane groups and the like.

As used herein, unless otherwise specified, the term "aryl" refers to an annular aromatic hydrocarbon substituent group.

The term "heteroaryl" refers to an aryl compound in which at least one carbon atom is replaced by an oxygen, a nitrogen or a sulphur atom. Examples of aryl or hetero aryl substituent groups include, without limitation, benzene, pyridine, pyrrole, quinolone, imidazole, triazine, pyrazine, pyrimidine, pyradazine, thiazine, dioxin, tetrazole, triazole, thiadiazole, pyrazole, oxazole, thiazole, furan and the like.

DESCRIPTION OF THE INVENTION

According to a first aspect of the invention, a compound characterized by a general formula (A) is provided:

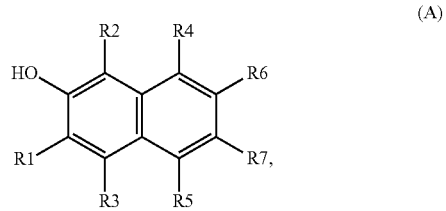

(A)

wherein

R$^1$ is selected from, —OH, —SH and —NH$_2$;

R$^2$ is selected from —NO$_2$, —SO$_3$H, —SO$_2$—OR$^{11}$, —SO$_2$—NH$_2$, —SO$_2$—NHR$^{11}$, —SO$_2$—NR$^{11}{}_2$, —PO$_3$H, —PO$_2$—OR$^{11}$, —CN, —COR$^{11}$, —CO$_2$R$^{11}$, —CONHR$^{11}$, —CONR$^{11}{}_2$, —CF$_3$, and halogen;

$R^3$ is selected from H, —$NO_2$, —$SO_3H$, —$SO_2$—$OR^{11}$, —$SO_2$—$NH_2$, —$SO_2$—$NHR^{11}$, —$SO_2$—$NR^{11}_2$, —$PO_3H$, —$PO_2$—$OR^{11}$, —CN, —$COR^{11}$, —$CO_2R^{11}$, —$CONHR^{11}$, —$CONR^{11}_2$, —$CF_3$ and halogen;

$R^4$ and $R^5$ are independently selected from —H, substituted $C_1$-$C_6$ alkyl, unsubstituted $C_1$-$C_6$ alkyl, substituted or unsubstituted $C_2$-$C_6$ alkenyl, substituted or unsubstituted $C_3$-$C_6$ cycloalkyl, halogen, —CN and —$NO_2$;

one of $R^6$ and $R^7$ is selected from —$CONR^9R^{11}$, —$CONR^9_2$, —$COR^9$, —$OCOR^9$, —$SO_2$—OH, —$SO_2R^9$, —$SO_2$—$OR^9$, —$SO_2$—$OR^{11}$, —$SO_2NHR^{11}$, —$SO_2NR^9R^{11}$, —$NO_2$, —CN, —$CF_3$ and —$SO_2NR^9_2$;

the other one of $R^6$ and $R^7$ is selected from H, —$CONH_2$, COOH, —$SO_2$—OH, —$SO_2NH_2$, —Y—$R^9$, —Y—$R^9_2$ and —$R^9$, wherein $R^9$ is $R^{10}$—(Y—$R^{10}$)$_n$ Y is selected from —$CONR^{11}$—, —CO—, —COO—, —$SO_3$—, —$SO_2NH$—, —$NR^{11}$—, —O—, —$NR^{11}CO$—, —OCO—, —$NR^{11}COO$—, —$NR^{11}CONR^{11}$—, —$OCONR^{11}$— and —OCOO— n is an integer selected from 0, 1, 2, 3 and 4, each $R^{10}$ independently of any other $R^{10}$ is selected from a substituted or unsubstituted $C_1$-$C_8$ alkyl, substituted or unsubstituted a $C_2$-$C_8$ alkenyl, a substituted or unsubstituted $C_2$-$C_8$ alkynyl, substituted or unsubstituted a $C_3$-$C_{10}$ cycloalkyl and a substituted or unsubstituted 5- to 10-membered aryl or heteroaryl; and each $R^{11}$ independently of any other $R^{11}$ is H or an unsubstituted $C_1$-$C_6$ alkyl.

In certain embodiments, $R^7$ is an electronegative, electron-withdrawing group selected from —$CONR^{11}R^9$, —$CONR^9_2$, —$COR^9$, —$COOR^9$, —$SO_2$—OH, —$SO_2R^9$, —$SO_2$—$OR^9$, —$SO_2NH_2$, —$SO_2$—$NHR^9$, —$SO_2NR^{11}R^9$, and —$SO_2NR^9_2$, and $R^9$ imparts steric hindrance on the "right" part of the molecule as viewed in the formula depiction, thus being free to take any form as defined for $R^9$ above.

In certain embodiments, $R^1$ is —OH, $R^2$ is —$NO_2$ and $R^3$ is H.

In certain embodiments, $R^1$ is —OH, $R^2$ is —$NO_2$ and $R^3$ is H, and $R^4$ and $R^5$ are H.

In certain embodiments, $R^1$ is —OH, $R^2$ is —$NO_2$ and $R^3$ is H, and $R^4$ and $R^5$ are H and $R^6$ is selected from H, —$CONH_2$, and —$CONR^9_2$ wherein $R^9$ has the same meaning as defined above.

In certain embodiments, $R^1$ is —OH, $R^2$ is —$NO_2$ and $R^3$ is H, and $R^4$ and $R^5$ are H and $R^7$ is selected from —$CONR^9_2$ and —$CONR^{11}R^9$, wherein $R^9$ and $R^{11}$ have the same meaning as defined above.

In certain embodiments, $R^1$ is —OH, $R^2$ is —$NO_2$ and $R^3$ is H, and $R^4$ and $R^5$ are H, $R^6$ is selected from H, —$CONH_2$, and —$CONR^9_2$ and $R^7$ is selected from —$CONR^9_2$ and —$CONR^{11}R^9$, wherein $R^9$ and $R^{11}$ have the same meaning as defined above.

In certain embodiments n is 0.

In certain embodiments n is 1.

In certain embodiments n is 2.

In certain embodiments $R^6$ is —$CONR^{11}R^{11}$, and $R^7$ is —$CONR^9R^{11}$, wherein each $R^{11}$ independently of any other $R^{11}$ is H or unsubstituted $C_1$-$C_4$ alkyl, and $R^9$ has the same meaning as defined above.

In certain embodiments, $R^1$ is —OH, $R^2$ is —$NO_2$ and $R^3$ is H, and $R^4$ and $R^5$ are H, $R^6$ is —$CONR^{11}R^{11}$, and $R^7$ is —$CONR^9R^{11}$, wherein each $R^{11}$ independently of any other $R^{11}$ is H or an unsubstituted $C_1$-$C_4$ alkyl, and $R^9$ has the same meaning as defined above.

In certain embodiments, $R^6$ and $R^7$ are —$CONR^9R^{11}$, and $R^9$ is $R^{11}$—(Y—$R^{10}$)$_n$, Y is selected from —$CONR^{11}$—, —$NR^{11}CO$—, —$NR^{11}COO$—, and —$NR^{11}CONR^{11}$—, n is 1 or 2, $R^{10}$ is an unsubstituted or monosubstituted $C_1$—, $C_2$—, $C_3$— or $C_4$ alkyl, $R^{11}$ is an unsubstituted $C_1$—, $C_2$—, $C_3$— or $C_4$ alkyl.

In certain embodiments, $R^1$ is —OH, $R^2$ is —$NO_2$ and $R^3$ is H, and $R^4$ and $R^5$ are H, $R^6$ and $R^7$ are —$CONR^9R^{11}$, and $R^9$ is $R^{11}$—(Y—$R^{10}$)$_n$, Y is selected from —$CONR^{11}$—, —$NR^{11}CO$—, —$NR^{11}COO$—, and —$NR^{11}CONR^{11}$—, n is 1 or 2, $R^{10}$ is an unsubstituted or monosubstituted $C_1$—, $C_2$—, $C_3$— or $C_4$ alkyl, $R^{11}$ is an unsubstituted $C_1$—, $C_2$—, $C_3$— or $C_4$ alkyl.

In certain embodiments, $R^6$ is —$CONR^{11}_2$ and $R^7$ is —$CONR^9R^{11}$, and $R^9$ is $R^{11}$—(Y—$R^{10}$)$_n$, Y is selected from —$CONR^{11}$—, —$NR^{11}CO$—, —$NR^{11}COO$—, and —$NR^{11}CONR^{11}$—, n is 1 or 2, $R^{10}$ is an unsubstituted or monosubstituted $C_1$—, $C_2$—, $C_3$— or $C_4$ alkyl, $R^{11}$ is an unsubstituted $C_1$—, $C_2$—, $C_3$— or $C_4$ alkyl.

In certain embodiments, $R^1$ is —OH, $R^2$ is —$NO_2$ and $R^3$ is H, $R^4$ and $R^5$ are H, $R^6$ is —$CONR^{11}_2$ and $R^7$ is —$CONR^9R^{11}$, and $R^9$ is $R^{11}$—(Y—$R^{10}$)$_n$, Y is selected from —$CONR^{11}$—, —$NR^{11}CO$—, —$NR^{11}COO$—, and —$NR^{11}CONR^{11}$—, n is 1 or 2, $R^{10}$ is an unsubstituted or monosubstituted $C_1$—, $C_2$—, $C_3$— or $C_4$ alkyl, $R^{11}$ is an unsubstituted $C_1$—, $C_2$—, $C_3$— or $C_4$ alkyl.

In certain embodiments, $R^6$ is H and $R^7$ is —$CONR^9R^{11}$, and $R^9$ is $R^{11}$—(Y—$R^{10}$)$_n$, Y is selected from —$CONR^{11}$—, —$NR^{11}CO$—, —$NR^{11}COO$—, and —$NR^{11}CONR^{11}$—, n is 1 or 2, $R^{10}$ is an unsubstituted or monosubstituted $C_1$—, $C_2$—, $C_3$— or $C_4$ alkyl, $R^{11}$ is an unsubstituted $C_1$—, $C_2$—, $C_3$— or $C_4$ alkyl.

In certain embodiments, $R^1$ is —OH, $R^2$ is —$NO_2$ and $R^3$ is H, $R^4$ and $R^5$ are H, $R^6$ is H and $R^7$ is —$CONR^9R^{11}$, and $R^9$ is $R^{11}$—(Y—$R^{10}$)$_n$, Y is selected from —$CONR^{11}$—, —$NR^{11}CO$—, —$NR^{11}COO$—, and —$NR^{11}CONR^{11}$—, n is 1 or 2, $R^{10}$ is an unsubstituted or monosubstituted $C_1$—, $C_2$—, $C_3$— or $C_4$ alkyl, $R^{11}$ is an unsubstituted $C_1$—, $C_2$—, $C_3$— or $C_4$ alkyl.

In certain embodiments, $R^7$ is —$CONR^9R^{11}$, and $R^9$ is $(CH_2)_4$—(Y—$R^{10}$)$_n$, Y is selected from —$CONR^{11}$—, —$NR^{11}CO$—, —$NR^{11}COO$—, and —$NR^{11}CONR^{11}$—, n is 1 or 2, $R^{10}$ is an unsubstituted or monosubstituted $C_1$—, $C_2$—, $C_3$— or $C_4$ alkyl, $R^{11}$ is an unsubstituted methyl or ethyl.

In certain embodiments, $R^1$ is —OH, $R^2$ is —NO$_2$ and $R^3$ is H, $R^4$ and $R^5$ are H, $R^6$ is H and $R^7$ is —CONR$^9$R$^{11}$, and
$R^9$ is (CH$_2$)$_4$—(Y—R$^{10}$)$_n$,
Y is selected from —CONR$^{11}$—, —NR$^{11}$CO—, —NR$^{11}$COO—, and —NR$^{11}$CONR$^{11}$—,
n is 1 or 2,
$R^{10}$ is an unsubstituted or monosubstituted C$_1$—, C$_2$—, C$_3$— or C$_4$ alkyl,
$R^{11}$ is an unsubstituted methyl or ethyl.

In certain embodiments, $R^1$ is —OH, $R^2$ is —NO$_2$ and $R^3$ is H, $R^4$ and $R^5$ are H, $R^6$ is —CONEt$_2$ and $R^7$ is —CONR$^9$R$^{11}$, and
$R^9$ is (CH$_2$)$_4$—(Y—R$^{10}$)$_n$,
Y is selected from —CONR$^{11}$—, —NR$^{11}$CO—, —NR$^{11}$COO—, and —NR$^{11}$CONR$^{11}$—,
n is 1 or 2,
$R^{10}$ is an unsubstituted or monosubstituted C$_1$—, C$_2$—, C$_3$— or C$_4$ alkyl,
$R^{11}$ is an unsubstituted methyl or ethyl.

In certain embodiments, a compound is provided selected from:

N2,N2,N3,N3-tetraethyl-6,7-dihydroxy-5-nitro-naphthalene-2,3-dicarboxamide (A1)

(A1)

(3-[[3-(diethylcarbamoyl)-6,7-dihydroxy-5-nitro-naphthalene-2-carbonyl]-ethyl-amino]propyl acetate) (A2)

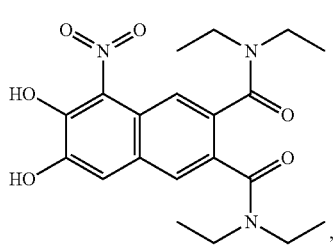

(A2)

N2-(6-aminohexyl)-N2,N3,N3-triethyl-6,7-dihydroxy-5-nitro-naphthalene-2,3-dicarboxamide (A4)

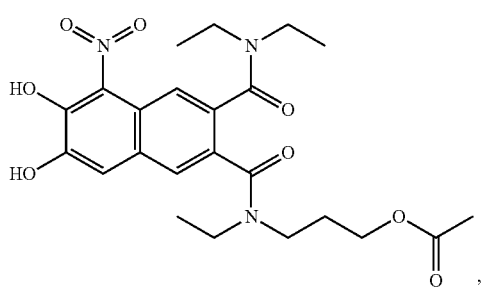

(A4)

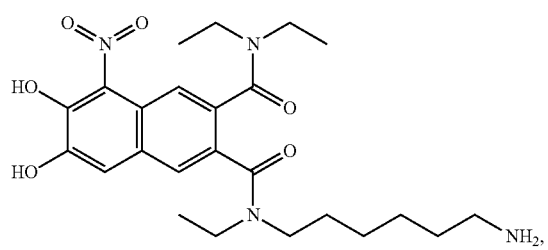

N2,N3,N3-triethyl-6,7-dihydroxy-N2-[4-[methyl(pentanoyl)amino]butyl]-5-nitro-naphthalene-2,3-dicarboxamide (A5)

(A5)

tert-butyl N-[6-[[3-(diethylcarbamoyl)-6,7-dihydroxy-5-nitro-naphthalene-2-

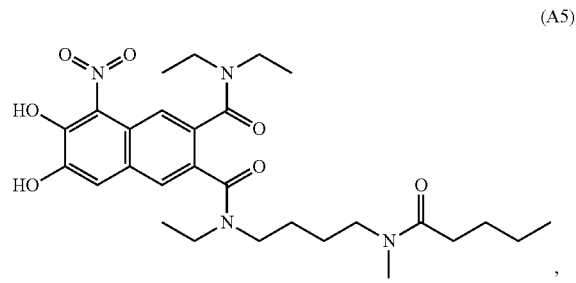 [SMILES: CCCCC(=O)N(C)CCCCN(CC)C(=O)c1cc2cc(O)c(O)c([N+](=O)[O-])c2cc1C(=O)N(CC)CC]

(A6)

4-[4-[[3-(diethylcarbamoyl)-6,7-dihydroxy-5-nitro-naphthalene-2-carbonyl]-ethyl-amino]butyl-methyl-amino]-4-oxo-butanoic acid (A8)

(A8)

N2-[4-[4-aminobutanoyl(methyl)amino]butyl]-N2,N3,N3-triethyl-6,7-dihydroxy-5-nitro-naphthalene-2,3-dicarboxamide (A9)

(A9)

tert-butyl N-[4-[4-[[3-(diethylcarbamoyl)-6,7-dihydroxy-5-nitro-naphthalene-2-

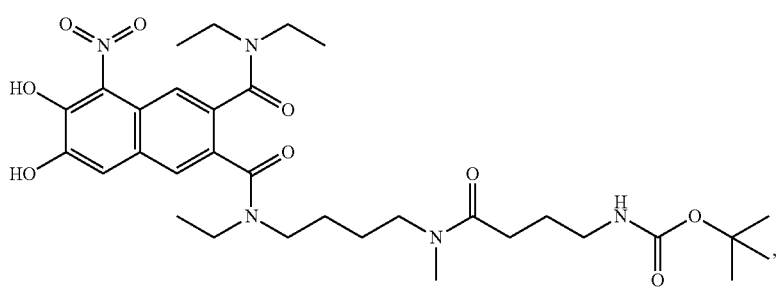
(A10)

N2,N3,N3-triethyl-6,7-dihydroxy-N2-[4-[[6-(2-methoxy-phenyl)-6-oxo-hexanoyl]-methyl-amino]butyl]-5-nitro-naphthalene-2,3-dicarboxamide (A11)

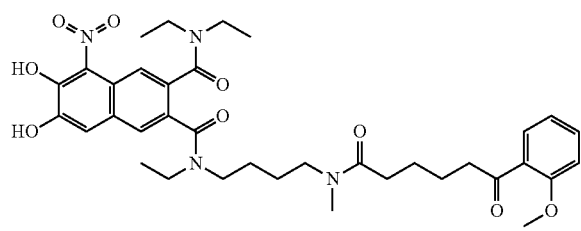
(A11)

and
tert-butyl N-[1-cyclohexyl-2-[4-[[3-(diethylcarbamoyl)-6,7-dihydroxy-5-nitro-naphthalene-2-carbonyl]-ethyl-amino]butyl-methyl-amino]-2-oxo-ethyl]carbamate (A13)

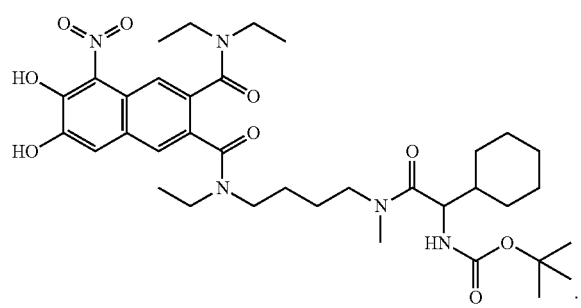
(A13)

According to another aspect of the invention, a compound characterized by a general formula (B) is provided, wherein
$R^8$ is selected from C, S, N, O, $NR^{11}$ and $CR^{11}$;
$R^1$, $R^2$, $R^3$, $R^9$ and $R^{11}$ have the same meaning as defined above.
In certain embodiments,
$R^1$ is —OH,
$R^2$ is —$NO_2$ and $R^3$ is H, and
$R^9$ is S;
and $R^9$ has the same meaning as defined above.
Certain embodiments are characterized by any one the formulae (B2), (B4), (B5), (B6), (B8), (B9), (B10), (B11) or (B13).

According to yet another aspect of the invention, a compound according to any one of the above disclosed aspects and embodiments of the invention is provided for use as a medicament.

According to yet another aspect of the invention, a compound according to any one of the above disclosed aspects and embodiments of the invention is provided for use as a medicament for use in prevention or treatment of a condition selected from the group comprising Parkinson's disease, Alzheimer's disease, multi-drug resistant tuberculosis and obesity-related disorders.

According to yet another aspect of the invention, a dosage form is provided comprising a compound according to any one of the above disclosed aspects and embodiments of the invention for use in the prevention or treatment of a condition selected from the group comprising Parkinson's disease, Alzheimer's disease, multi-drug resistant tuberculosis and obesity-related disorders; wherein said dosage form is suitable for inhalation or oral administration, in particular said dosage form is a tablet, capsule, lozenge, powder, solution, suspension or syrup.

According to yet another aspect of the invention, an inhibitor of COMT is provided for use in the prevention or treatment of a condition selected from the group comprising Parkinson's disease, Alzheimer's disease, multi-drug resistant tuberculosis and obesity-related disorders, characterized in that said inhibitor does not bind to HIBCH.

Further aspects and embodiments of the invention are disclosed in the following items:
Item 1: A compound characterized by a general formula (B)

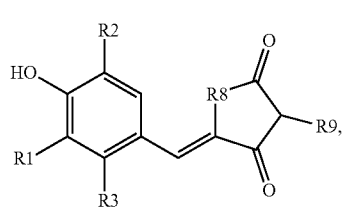
(B)

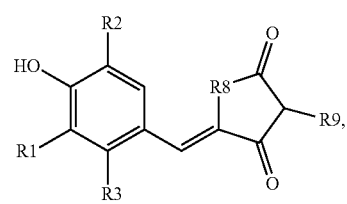
(B)

wherein
R$^1$ is selected from, —OH, —SH and —NH$_2$;
R$^2$ is selected from —NO$_2$, —SO$_3$H, —SO$_2$—OR$^{11}$, —SO$_2$—NH$_2$, —SO$_2$—NHR$^{11}$, —SO$_2$—NR$^{11}{}_2$, —PO$_3$H, —PO$_2$—OR$^{11}$, —CN, —COR$^{11}$, —CO$_2$R$^{11}$, —CONHR$^{11}$, —CONR$^{11}{}_2$, —CF$_3$, and halogen;
R$^3$ is selected from H, —NO$_2$, —SO$_3$H, —SO$_2$—OR$^{11}$, —SO$_2$—NH$_2$, —SO$_2$—NHR$^{11}$, —SO$_2$—NR$^{11}{}_2$, —PO$_3$H, —PO$_2$—OR$^{11}$, —CN, —COR$^{11}$, —CO$_2$R$^{11}$, —CONHR$^{11}$, —CONR$^{11}{}_2$, —CF$_3$, and halogen;
R$^8$ is selected from C, S, N, O, NR$^{11}$ and CR$^{11}$;
R$^9$ is R$^{10}$—(Y—R$^{10}$)$_n$
Y is selected from —CONR$^{11}$—, —CO—, —COO—, —SO$_3$—, —SO$_2$NH—, —NR$^{11}$—, —O—, —NR$^{11}$CO—, —OCO—, —NR$^{11}$COO—, —NR$^{11}$CONR$^{11}$—, —OCONR$^{11}$— and —OCOO—
n is an integer selected from 0, 1, 2, 3 and 4,
each R$^{10}$ independently of any other R$^{10}$ is selected from a substituted or unsubstituted C$_1$-C$_8$ alkyl, substituted or unsubstituted a C$_2$-C$_8$ alkenyl, a substituted or unsubstituted C$_2$-C$_8$ alkynyl, substituted or unsubstituted a C$_3$-C$_{10}$ cycloalkyl and a substituted or unsubstituted 5- to 10-membered aryl or heteroaryl; and each R$^{11}$ independently of any other R$^{11}$ is H or an unsubstituted C$_1$-C$_6$ alkyl.

Item 2: The compound characterized by the general formula (B) of item 1, wherein
R$^1$ is —OH,
R$^2$ is —NO$_2$ and R$^3$ is H, and
R$^8$ is S;
and R$^9$ has the same meaning as defined for item 1.
Item 3: The compound of items 1 or 2, wherein n is 0.
Item 4: The compound of items 1 or 2, wherein n is 1.
Item 5: The compound of items 1 or 2, wherein n is 2.
Item 6: The compound of items 1 or 2, wherein n is 3.
Item 7: The compound of any one of items 1 to 6, wherein
R$^9$ is R$^{11}$—(Y—R$^{10}$)$_n$
Y is selected from —CONR$^{11}$—, —NR$^{11}$CO—, —NR$^{11}$COO—, and —NR$^{11}$CONR$^{11}$—,
n is 1 or 2,
R$^{10}$ is an unsubstituted or monosubstituted C$_1$—, C$_2$—, C$_3$— or C$_4$ alkyl,
R$^{11}$ is an unsubstituted C$_1$—, C$_2$—, C$_3$— or C$_4$ alkyl.
Item 8: The compound of any one of items 1 to 7, wherein
R$^9$ is (CH$_2$)$_4$—(Y—R$^{10}$)$_n$,
Y is selected from —CONR$^{11}$—, —NR$^{11}$CO—, —NR$^{11}$COO—, and —NR$^{11}$CONR$^{11}$—,
n is 1 or 2,
R$^{10}$ is an unsubstituted or monosubstituted C$_1$—, C$_2$—, C$_3$— or C$_4$ alkyl,
R$^{11}$ is an unsubstituted methyl or ethyl.
Further embodiments are the following formulae:

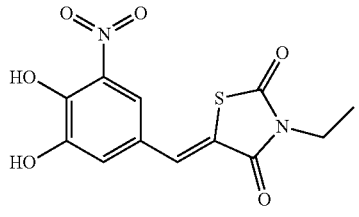

CPT-212
(5Z)-5-[(3,4-dihydroxy-5-nitro-phenyl)methylene]-3-ethyl-thiazolidine-2,4-dione
(B1)

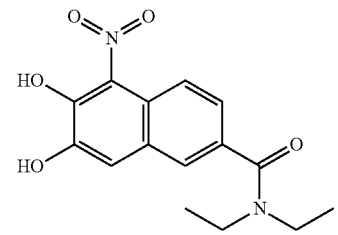

N,N-diethyl-6,7-dihydroxy-5-nitro-naphthalene-2-carboxamide
(A1.2)

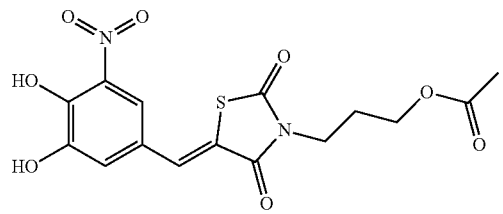

3-[(5Z)-5-[(3,4-dihydroxy-5-nitro-phenyl)methylene]2,4-dioxo-thiazolidin-3-yl]propyl acetate
(B2)

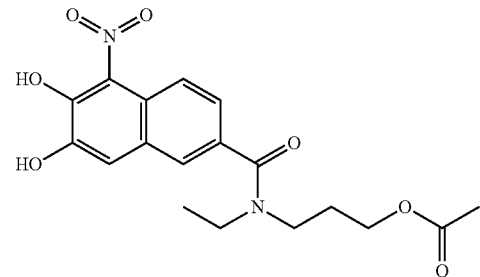

3-[(6,7-dihydroxy-5-nitro-naphthalene-2-carbonyl)-ethyl-amino]propyl acetate
(A2.2)

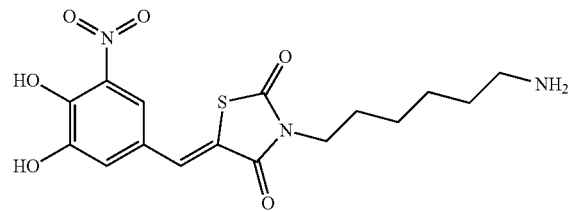

(5Z)-3-(6-aminohexyl)-5-[(3,4-dihydroxy-5-nitro-phenyl)methylene]thiazolidine-2,4-dione
(B4)

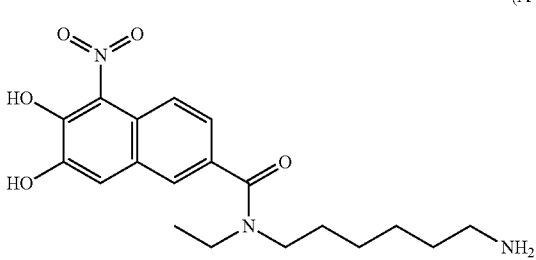

N-(6-aminohexyl)-N-ethyl-6,7-dihydroxy-5-nitro-naphthalene-2-carboxamide
(A4.2)

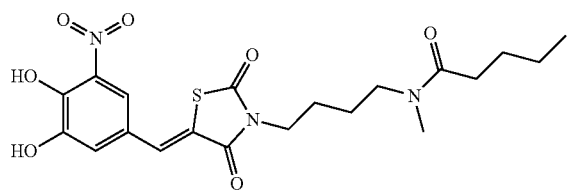

N-[4-[(5Z)-5-[(3,4-dihydroxy-5-nitro-phenyl)methylene]-2,4-dioxo-thiazolidin-3-yl]butyl]-N-methyl-pentanamide
(B5)

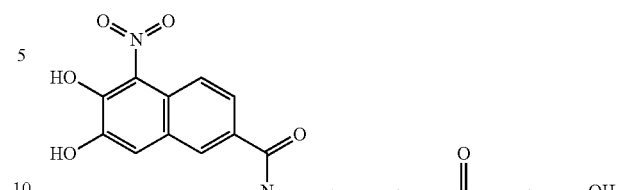

4-[4-[(6,7-dihydroxy-5-nitro-naphthalene-2-carbonyl)-ethyl-amino]butylamino]-4-oxo-butanoic acid
(A8.2)

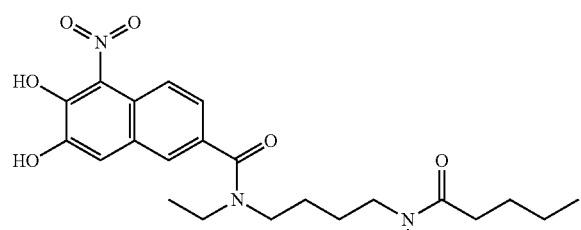

N-ethyl-6,7-dihydroxy-N-[4-[methyl(pentanoyl)amino]butyl]-5-nitro-naphthalene-2-carboxamide
(A5.2)

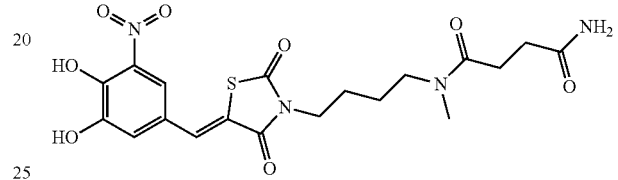

4-amino-N-[4-[(5Z)-5-[(3,4-dihydroxy-5-nitro-phenyl)methylene]-2,4-dioxo-thiazolidin-3-yl]butyl]-N-methyl-butanamide
(B9)

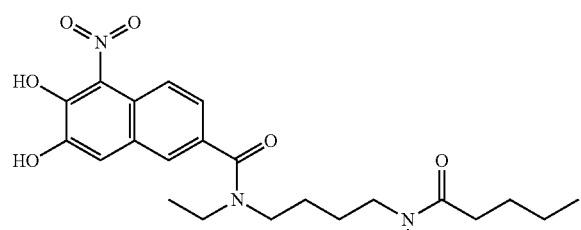

tert-butyl N-[6-[(5Z)-5-[(3,4-dihydroxy-5-nitro-phenyl)methylene]-2,4-dioxo-thiazolidin-3-yl]hexyl]carbamate
(B6)

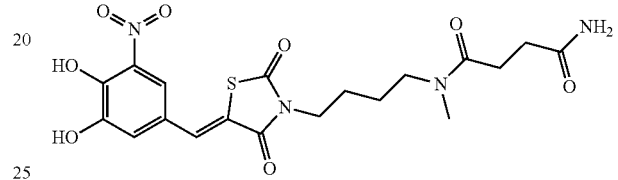

N-[4-[4-aminobutanoyl(methyl)amino]butyl]-N-ethyl-6,7-dihydroxy-5-nitro-naphthalene-2-carboxamide
(A9.2)

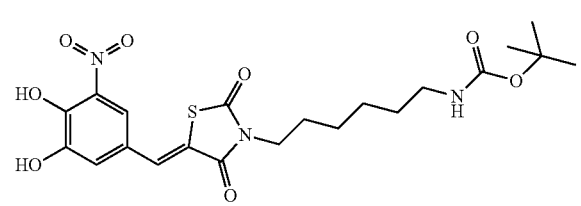

tert-butyl N-[6-[(6,7-dihydroxy-5-nitro-naphthalene-2-carbonyl)-ethyl-amino]hexyl]carbamate
(A6.2)

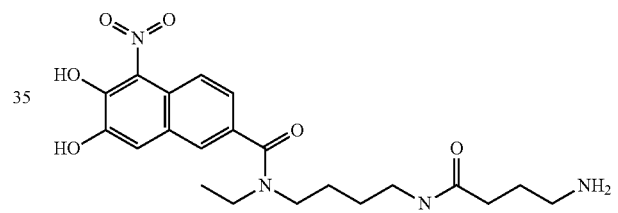

tert-butyl N-[4-[4-[(5Z)-5-[(3,4-dihydroxy-5-nitro-phenyl)methylene]-2,4-dioxo-thiazolidin-3-yl]butyl-methyl-amino]-4-oxo-butyl]carbamate
(B10)

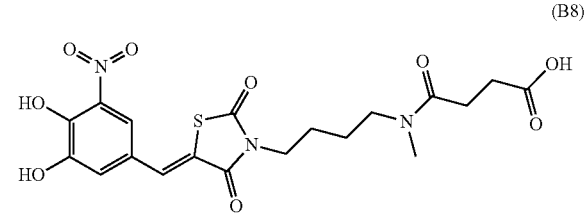

4-[4-[(5Z)-5-[(3,4-dihydroxy-5-nitro-phenyl)methylene]-2,4-dioxo-thiazolidin-3-yl]butyl-methyl-amino]-4-oxo-butanoic acid
(B8)

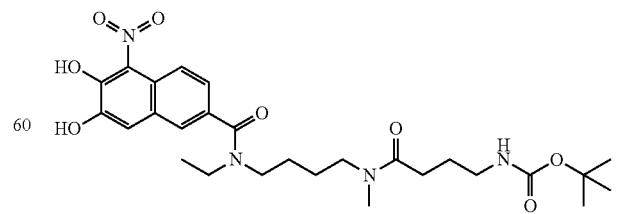

tert-butyl N-[4-[4-[(6,7-dihydroxy-5-nitro-naphthalene-2-carbonyl)-ethyl-amino]butyl-methyl-amino]-4-oxo-butyl]carbamate
(A10.2)

-continued

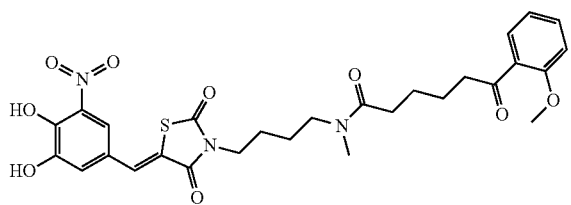

(B11)

N-[4-[(5Z)-5-[(3,4-dihydroxy-5-nitro-phenyl)methylene]-2,4-dioxo-thiazolidin-3-yl]butyl]-6-(2-methoxyphenyl)-N-methyl-6-oxo-hexanamide

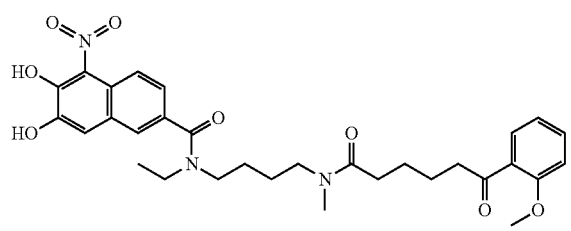

(A11.2)

N-ethyl-6,7-dihydroxy-N-[4-[[6-(2-methoxyphenyl)-6-oxo-hexanoyl]methyl-amino]butyl]-5-nitro-naphthalene-2-carboxamide

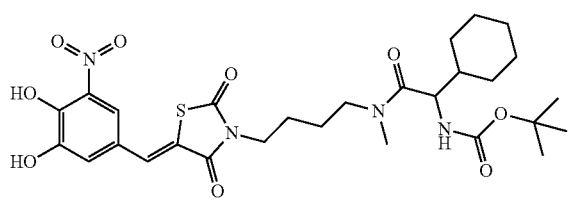

(B13)

tert-butyl N-[1-cyclohexyl-2-[4-[(5Z)-5-[(3,4-dihydroxy-5-nitro-phenyl)methylene]-2,4-dioxo-thiazolidin-3-yl]butyl-methyl-amino]-2-oxo-ethyl]carbamate

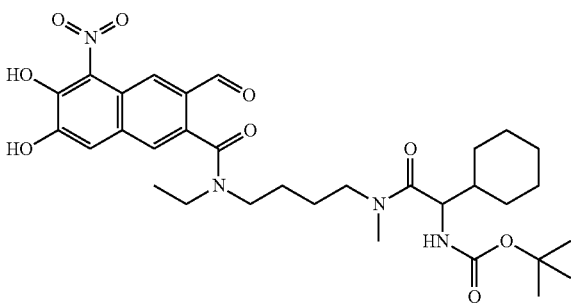

(A13.2)

tert-butyl N-[1-cyclohexyl-2-[4-[ethyl-(3-formyl-6,7-dihydroxy-5-nitro-naphthalene-2-carbonyl)amino]butyl-methyl-amino]-2-oxo-ethyl]carbamate In the experimental work leading up to the present invention, two small molecules, CPT-401 (A1), and CPT-212 (B1), were synthesized as the lead COMT inhibitors to be compared with tolcapone and entacapone (FIG. 1). The inventors compared the inhibition of COMT by tolcapone, entacapone and derivatives of CPT-401 (A1) and CPT-212 (B1) (FIG. 9). The results show that the side chains can vary without impairing the COMT inhibition.

Subsequently, the four compounds tolcapone, entacapone, CPT-401 (A1) and CPT-212 (B1) were compared with regard to off-target binding.

Structurally related inhibitors of a shared therapeutic target may differ regarding potential toxicity issues that are caused by differential off-target binding. A cause underlying the hepatotoxic effect of tolcapone may be its off-target binding to the enzyme 3-Hydroxyisobutyryl-CoA hydrolase (HIBCH, CAS NO 9025-88-1). The HIBCH enzyme is crucial to prevent the accumulation of toxic methacrylyl-CoA by removing CoA from 3-hydroxyisobutyryl-CoA in the valine catabolic pathway and reduced enzyme activity in human livers has been correlated with liver cirrhosis and hepatocellular carcinoma, suggesting that a decrease in the capability to dispose methacrylyl-CoA could lead to liver failure. Thus, inhibition of HIBCH leads to accumulation of methacrylyl-CoA, which is cytotoxic. The identification of this protein as a tolcapone-specific off-target provides a novel possible explanation for tolcapone-induced toxic effects in liver. When binding to HIBCH, tolcapone adopts a conformation in which the two aromatic moieties are tilted against each other. In contrast, CPT-401 and entacapone are characterized by a relative planarity. Thus, their binding to HIBCH is prevented.

Catechol O-methyltransferase (COMT, EC 2.1.1.6) exists in two forms, the soluble form (S-COMT) and membrane-bound form (MB-COMT). As cytosolic protein, S-COMT is the predominant form in most tissues and plays a more important role in inactivation of endogenous and xenobiotic catechols. Rat and human COMT share 81% sequence identity and both belong to the highly structurally conserved SAM-dependent methyltransferase fold family. Since the main focus of the present invention is the potency of the novel COMT inhibitors in human, in-house overexpressed recombinant human COMT protein (see experimental procedures) was used in the inhibition assay. The assay method described previously (Kurkela, Anal Biochem, 2004. 331(1): 198-200) was applied, in which the methylation of the substrate aesculetin to scopoletin in a reaction mixture in presence of S-(5-adenosyl)-L-methionine (AdoMet) was measured fluorometrically.

FIG. 2 shows the COMT inhibition curves of the compounds CPT-401 (A1), CPT-212 (B1). Tolcapone and entacapone were included in the inhibition assay as reference. It was reported that entacapone has an $IC_{50}$ of 160 nM and tolcapone has an $IC_{50}$ of 36 nM in rat liver homogenate (Kiss, J Med Chem, 2014. 57(21): 8692-717). In the used assay, tolcapone again was found to be more potent under in vitro experimental conditions than entacapone with human recombinant COMT, with $IC_{50}$ values of 53 nM for tolcapone and 386 nM for entacapone, respectively. Lead compound CPT-401 (A1) showed an activity similar to tolcapone with an IC50 of 54 nM, and CPT-212 (B1) revealed an IC50 of 179 nM in the assay. Thus, the inhibition of COMT by CPT-401 (A1) was similar to that of tolcapone. CPT-212 (B1) exhibited a COMT inhibition higher than entacapone, but significantly lower than CPT-401 (A1) and tolcapone (see FIG. 2).

Side-effects are often caused by off-target binding of a drug to other proteins. The severe side-effects of tolcapone in comparison to entacapone are likely due to the interaction of certain proteins with tolcapone, but not entacapone. Thus, the inventors identified proteins that interact with tolcapone, but not entacapone using differential competition Capture Compound Mass Spectrometry (dCCMS). For details reference is made to the experimental section.

The enzyme 3-Hydroxyisobutyryl-CoA hydrolase (HIBCH) was identified to bind tolcapone and CPT-212 (B1), but not entacapone and CPT-401 (A1) (FIG. 5, FIG. 6). This can be explained by common structural features of the two molecule pairs: Tolcapone and CPT-212 (B1) adopt a conformation where the two aromatic moieties are tilted against each other. This conformation neatly fits into the HIBCH binding pocket (data not shown). Entacapone—and even more CPT-401 (A1)—prefer or are restricted to an overall planar conformation.

The inventors compared the mitochondrial cytotoxicity of tolcapone, entacapone, CPT-401 (A1) and CPT-212 (B1). It was demonstrated that the mitochondrial cytotoxicity of tolcapone and CPT-212 (B1) is significantly higher than that of entacapone and CPT-401 (A1) (FIG. 7).

The compound of the present invention, new COMT inhibitor CPT-401 (A1), exhibits reduced off-target binding compared to tolcapone and increased potency compared to entacapone. Thus, it is a potent novel COMT inhibitor with low mitochondrial cytotoxicity and a promising compound for therapy of Parkinson's disease.

Other indications for the compound of the present invention are Alzheimer's disease, multi-drug resistant tuberculosis and obesity and metabolic disease.

In addition to inhibition of COMT, entacapone and tolcapone have been shown to inhibit aggregation of α-synuclein monomers. This constitutes a second beneficial effect in the treatment of Parkinson's disease.

COMT inhibitors entacapone and tolcapone have also been shown to inhibit the aggregation of Aβ42 protofibrils to mature amyloid fibrils, possibly by direct interaction with the protofibrils (Di Giovanni, J Biol Chem. 2010 May 14; 285(20):14941-54). Thus, CPT-401 (A1) might be used for therapy and prevention of Alzheimer's disease.

COMT inhibitors tolcapone and entacapone have been shown to bind and inhibit enoyl-acyl carrier protein reductase (InhA), an enzyme targeted by existing tuberculosis drugs (Kinnings, PLoS Comput Biol. 2009 July; 5(7): e1000423). InhA is essential for the biosynthesis of type II fatty acids and the subsequent building of the bacterial cell wall. Existing drugs for tuberculosis like isoniazid and ethionamid bind the same target, but have a completely different chemical structure and can elicit severe side effects. In addition, bacterial resistance mechanisms against these drugs are increasingly observed. Thus, CPT-401 (A1) might be used for the treatment of multi-drug resistant (MDR) and extensively drug resistant (XDR) tuberculosis.

COMT inhibitor entacapone has been shown to bind and inhibit the fat mass and obesity-associated gene product (FTO). Administration of entacapone leads to reduced triglyceride synthesis, reduced body weight and reduced serum cholesterol levels (WO2014082544). Thus, CTP-401 (A1) might be used for obesity treatment.

Experimental Section:
Synthesis:
Unless otherwise noted, all reactions were performed in dried glassware under argon. Commercially available high grade reagents and solvents were used as received without further purification. Column chromatography was carried out on a "CombiFlash" Companion system from Teledyne Isco., using pre-packed "GraceResolv™ Silica" columns as stationary phase. MPLC purification was performed on a Buechi system (Buechi control unit C-620; two Buechi pump modules C-605; column—omnifit (230×15 mm); stationary phase—LiChroprep RP-select B 25-40 µm; Buechi UV photometer C-635; Buechi fraction collector C-660; mobile phase A: 0.1% AcOH (Millipore grade); mobile phase B: MeCN (prepsolv grade). LC-MS was carried out on a Dionex Ultimate 3000 RS HPLC coupled to a Bruker amaZon Speed ion trap via an ESI source. LC method: compounds were diluted to about 5 µM in 20% MeCN, of which 50 µL were injected. Samples were separated on a Phenomenex Luna PFP column (50×2 mm, 3 µm, 100 Å), with a linear gradient of 10% to 100% B in 5.5 min. Mobile phase A: 0.1% HCOOH (Millipore grade); mobile phase B: MeCN (LC MS grade). Proton nuclear magnetic resonance (1H NMR) spectra and carbon nuclear magnetic resonance (13C NMR) spectra were recorded on an Avance 400 (400 MHz) from Bruker. Chemical shifts are reported in ppm relative to d-DMSO (δ 2.50) and CDCl3 (δ 7.27) for 1H NMR.

The synthesis of the two novel inhibitors CPT-401 (A1) and CPT-212 (B1) are depicted in Scheme 1 and 2, respectively.

Compound CPT-212 (B1) was accessible by piperidine promoted condensation reaction (US2006142303, incorporated herein by reference) of alkyl thiazolidine-2,4-dione derivative 3 with commercially available 3,4-dihydroxy-5-nitrobenzaldehyde 1 (Scheme 1).

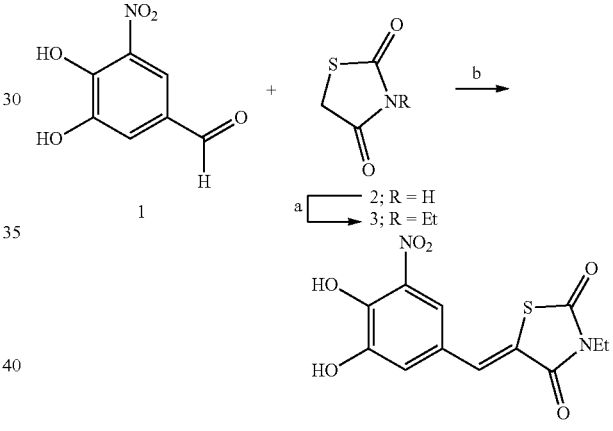

Scheme 1. Synthesis of novel COMT inhibitor CPT-212.

Reagents and conditions: (a) ethyl bromide, DIPEA, DMF, 23° C., 4 days, 89%; (b) piperidine, MeOH, 80° C., 17 h, 66%.

Bicyclic nitro-catechol CPT-401 (A1) was synthesized in eight synthetic steps starting from commercially available 3,4-dimethoxybenzoic acid 4 (Scheme 2).

Compound 4 was converted into bis-alcohol 6 by subsequent cyclisation reaction with formaldehyde under acid conditions and reductive ring-opening (Maziane, Tetrahedron Letters, 2001, 42 (6), 1017-1020). An alternative route starting from 1,2-bis(chloromethyl)-4,5-dimethoxybenzene and subsequent double substitution with acetic acid and saponification seems to be more practicable but was lower in yield. Whereas Swern oxidation of bis-alcohol 6 gave bis-aldehyde 7 in good yields, manganese dioxide promoted oxidation mainly yielded lactone 5. Bis-aldehyde 7 was then converted into tricyclic compound 9 via tetrabromide 8 and cyclisation reaction with maleic anhydride (McOmie, Synthesis, 1973, 416-417). Anhydride 9 was ring-opened with dimethyl amine to form a monoamide intermediate and screening of potential coupling reagents indicated HATU to be superior in yielding bis-amide 10 at 62% over both synthetic steps. Boron tribromide promoted double ether cleavage delivered 11 (Naito, Chemical & Pharmaceutical Bulletin, 1991, 39 (7), 1736-1745), which was converted into nitro-catechol CPT-401 (A1) by selective introduction of one nitro group (Lemaire, Tetrahedron, 43 (5), 835-844). For the latter conversion, both nitric acid and ACN seam not to work as expected, and 2,3,5,6-tetrabromo-4-methyl-4-nitrocyclohexa-2,5-dienone mainly gave a double nitro side-product. Careful titration of the amount of reagent finally gave the desired product in moderate yields. The structure of CPT-401 (A1) could be confirmed by two-dimensional NMR spectroscopy and mass spectrometry.

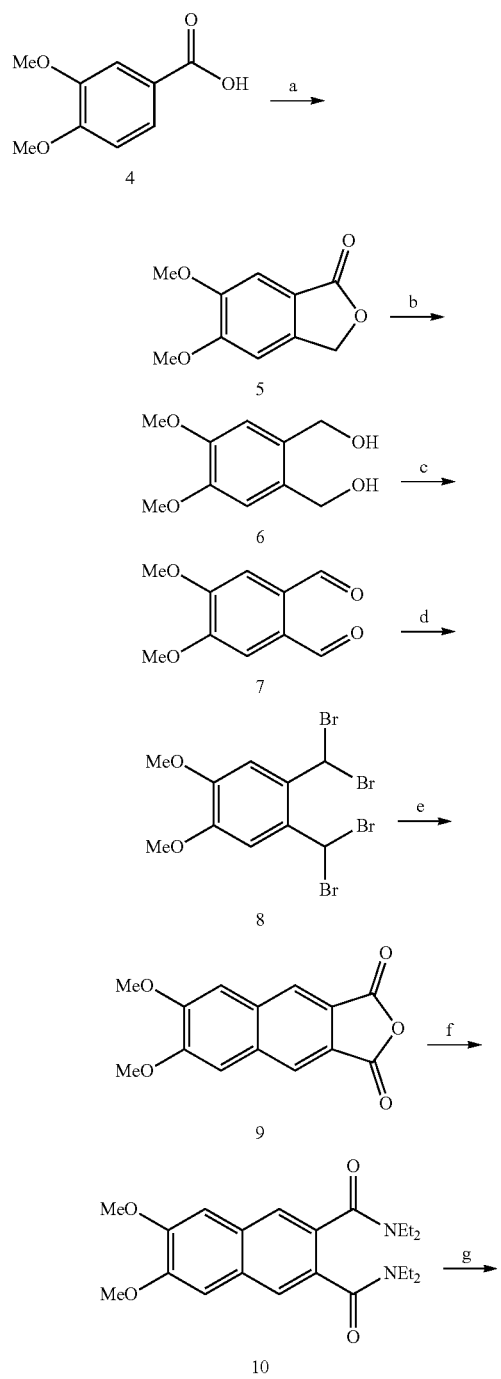

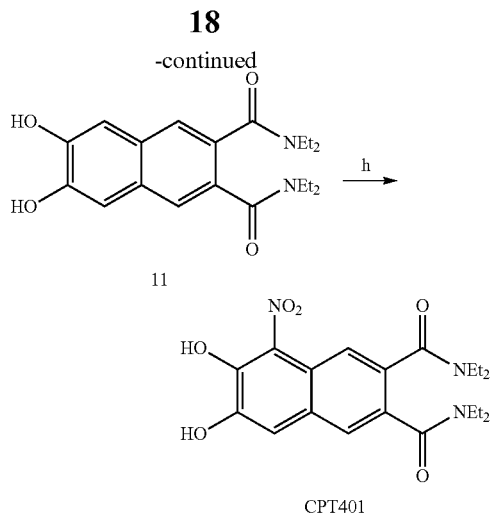

(A1). Reagents and conditions: (a) formaldehyde, HCl (gas), 70° C., 4 days, 93%; (b) LiAlH₄, THF, 66° C., 4 h, 77%; (c) oxalyl chloride, DMSO, TEA, DCM, -78° C., 105 min → 23° C., 60 min, 75%; (d) PBr₅, benzene, 23° C., 60 min, 41%; (e) maleic anhydride, NaI, DMF, 70° C., 48 h, 69%; (f) diethyl amine, HATU, DIPEA, DMF, 23° C., 48 h, 62%; (g) BBr₃, DCM, 0° C., 20 min → 23° C., 60 min, 98%; (h) 2,3,5,6-tetrabromo-4-methyl-4-nitrocyclohexa-2,5-dienone, diethyl ether, 23° C., 60 min, 55%.

Compound 3.

A solution of thiazolidine-2,4-dione 2 (500 mg; 4.27 mmol) and ethyl bromide (465 mg; 4.27 mmol) in dry DMF (11.4 mL) was treated with DIPEA (2.23 mL; 12.81 mmol) and stirred for 17 h at 23° C. Since TLC indicated incomplete conversion, another batch of ethyl bromide (465 mg; 4.27 mmol) was added and the reaction mixture was stirred for additionally 3 days at 23° C. All volatiles were removed under reduced pressure and the crude product was purified by CombiFlash (cyclohexane/EtOAc, 99/1 to 3/1) to obtain compound 3 (550 mg; 3.79 mmol; 89%) as a colorless liquid. $^1$H NMR (CDCl$_3$): δ 3.94 (s, 2H), 3.69 (q, J=7.1 Hz, 2H), 1.20 (t, J=7.1 Hz, 3H).

Compound CPT-212 (B1).

A solution of 3,4-dihydroxy-5-nitrobenzaldehyde 1 (185 mg; 1.01 mmol) and compound 3 (148 mg; 1.02 mmol) in dry MeOH (2.5 mL) was treated with piperidine (155 μL; 1.57 mmol) and stirred for 17 h at 80° C. The reaction mixture was diluted with ethyl acetate and washed twice with 0.5 M HCl solution. The organic layer was dried over Mg$_2$SO$_4$ and all solvents were removed under reduced pressure. The crude product was re-crystallized from MeOH to obtain nitro-catechol CPT-212 (207 mg; 0.67 mmol; 66%) as a yellow solid. $^1$H NMR (CDCl$_3$): δ 10.85 (s, 1H), 7.84 (s, 1H), 7.76 (s, 1H), 7.38 (s, 1H), 6.09 (s, 1H), 3.83 (q, J=7.1 Hz, 2H), 1.28 (t, J=7.1 Hz, 3H). LC-MS: r$_t$=3.27 min; 308.83 [M−H]$^-$; 640.92 [2M+Na−2H]$^-$.

Compound 5.

At 0° C., HCl gas was bubbled through a solution of formaldehyde (37% in water; 90 mL; 1.2 mol) for 30 min. 3,4-dimethoxybenzoic acid 4 (10 g; 54.9 mmol) was added and the reaction mixture was heated to 70° C., while HCl gas was continued to bubble through the suspension. After 3 days, all volatiles were removed under reduced pressure and water (200 mL) was added. The pH was adjusted to pH=7 by addition of aqueous NH$_3$ solution. The solid product was separated by filtration and dried under reduced pressure to yield lactone 5 (9.88 g; 50.9 mmol; 93%) as an off-white solid. $^1$H NMR (d-DMSO): δ 7.26 (s, 1H), 7.23 (s, 1H), 5.27 (s, 2H), 3.87 (s, 3H), 3.84 (s, 3H).

Compound 6.

A solution of lactone 5 (7.0 g; 36.0 mmol) in dry THF (170 mL) was added drop-wise to a suspension of lithium aluminium hydride (3.67 g; 108 mmol) in dry THF (50 mL). The reaction mixture was stirred for 4 h at 66° C. After cooling to 0° C., the reaction was carefully quenched by subsequent addition of water (7 mL) and 5 M NaOH solution (7 mL). The solid was discarded after filtration and all solvents were removed under reduced pressure. Water was added and the product was extensively extracted with DCM. The combined organic layers were dried over $Mg_2SO_4$ and DCM was removed under reduced pressure to give alcohol 6 (5.5 g; 27.7 mmol; 77%). $^1$H NMR (d-DMSO): δ 6.98 (s, 2H), 4.99 (br, s, 2H), 4.47 (s, 4H), 3.74 (s, 6H).

Compound 7.

At −78° C., a solution of alcohol 6 (2.2 g; 11.1 mmol) in dry DCM (25 mL) was added to a pre-stirred solution of oxalyl chloride (1.94 mL; 22.2 mmol) and DMSO (3.47 mL; 48.8 mmol) in dry DCM (55 mL) and stirred for 45 min at −78° C. Triethylamine (21.84 mL; 155 mmol) was added drop-wise and the reaction mixture was stirred additional 60 min at −78° C., was then allowed to warm to 23° C. and stirred additional 60 min. The reaction was carefully quenched by addition of water (200 mL) and the product was extracted with DCM. The combined organic layers were washed with ammonium chloride solution, dried over $Mg_2SO_4$ and the solvent was removed under reduced pressure to yield aldehyde 7 (1.62 g; 8.36 mmol; 75%). $^1$H NMR (d-DMSO): δ 10.52 (s, 2H), 7.54 (s, 2H), 3.94 (s, 6H).

Compound 8.

A solution of aldehyde 7 (1.6 g; 8.24 mmol) in dry benzene (55 mL) was treated with pentabromophosphorane (8.87 g; 20.6 mmol) and stirred for 17 h at 23° C. The reaction was carefully quenched by addition of 1% KOH solution (50 mL). The layers were separated and the water layer was extracted twice with DCM. The combined organic layers were washed with brine, dried over $Mg_2SO_4$ and all solvents were removed under reduced pressure. The crude product was purified by CombiFlash (cyclohexane/EtOAc, 9/1 to 1/1) to obtain bromide 8 (1.61 g; 3.34 mmol; 41%). $^1$H NMR (CDCl$_3$): δ 7.10 (br, s, 4H), 3.93 (s, 6H).

Compound 9.

A solution of bromide 8 (1.6 g; 3.32 mmol) and maleic anhydride (0.78 g; 7.97 mmol) in dry DMF (20 mL) was treated with sodium iodide (2.34 g; 15.61 mmol) and stirred for 48 h at 70° C. The reaction was quenched by addition of water (100 mL) and saturated $Na_2SO_3$ solution (20 mL). Solid product 9 (591 mg; 2.29 mmol; 69%) was obtained after filtration and drying under reduced pressure. $^1$H NMR (d-DMSO): δ 8.52 (s, 2H), 7.76 (s, 2H), 3.97 (s, 6H).

Compound 10.

A solution of tri-cyclic compound 9 (171 mg; 0.662 mmol) in dry DMF (200 μL) was treated with diethyl amine (152 μL; 1.46 mmol) and stirred for 1 h at 23° C. HATU (302 mg; 0.80 mmol) and DIPEA (231 μL; 1.32 mmol) were added and stirring was continued for 48 h at 23° C. All volatiles were removed under reduced pressure and the crude product was purified by MPLC (water/acetonitrile, 4/1 to 1/1) to obtain bis-amide 10 (158 mg; 0.409 mmol; 62%). $^1$H NMR (CDCl$_3$): δ 7.59 (s, 2H), 7.10 (s, 2H), 4.01 (s, 6H), 3.52 (q, J=7.1 Hz, 4H), 3.31 (q, J=7.1 Hz, 4H), 1.24 (t, J=7.1 Hz, 6H), 1.10 (t, J=7.1 Hz, 6H).

Compound 11.

At 0° C., a solution of bis-amide 10 (158 mg; 0.409 mmol) in dry DCM (16 mL) was treated with BBr$_3$ solution (1 M in DCM; 2.04 mL; 2.04 mmol). The reaction mixture was stirred for 20 min at 0° C., was allowed to warm to 23° C. and was stirred additionally 60 min. All volatiles were removed by nitrogen stream and the crude product was purified by MPLC (water/acetonitrile, 4/1 to 1/9) to obtain bis-amide 11 (143 mg; 0.399 mmol; 98%). $^1$H NMR (d-DMSO): δ 9.73 (br, s, 2H), 7.50 (s, 2H), 7.17 (s, 2H), 3.37 (q, J=6.8 Hz, 4H), 3.15 (q, J=6.8 Hz, 4H), 1.09 (t, J=6.8 Hz, 6H), 1.04 (t, J=6.8 Hz, 6H). $^1$H NMR (CDCl$_3$): δ 8.11 (br, s, 2H), 6.83 (s, 2H), 3.54 (q, J=6.4 Hz, 4H), 3.27 (q, J=6.4 Hz, 4H), 1.25 (t, J=6.4 Hz, 6H), 1.07 (t, J=6.4 Hz, 6H).

Compound CPT-401 (A1).

A solution of bis-amide 11 (15.0 mg; 0.042 mmol) in dry diethyl ether (2 mL) was subsequently treated three times with solutions of 2,3,5,6-tetrabromo-4-methyl-4-nitrocyclohexa-2,5-dienone (9.81 mg; 0.021 mmol) in dry diethyl ether (1 mL) and stirred for 20 min at 23° C. Since TLC indicated full conversion, all volatiles were removed by nitrogen stream and the crude product was purified by MPLC (water/acetonitrile, 9/1 to 3/1) to obtain nitro-catechol CPT-401 (9.2 mg; 0.023 mmol; 55%). $^1$H NMR (CDCl$_3$): δ 12.55 (br, s, 1H), 8.76 (s, 1H), 7.58 (s, 1H), 7.50 (s, 1H), 3.55-3.32 (m, 4H), 3.29 (q, J=7.2 Hz, 4H), 1.24 (t, J=6.9 Hz, 6H), 1.16 (t, J=7.2 Hz, 3H), 1.12 (t, J=7.2 Hz, 3H). LC-MS: r$_t$=2.66 min; 330.98 [M-N(CH$_2$CH$_3$)$_2$]$^+$; 404.07 [M+H]$^+$; 807.15 [2M+H]$^+$; 829.27 [2M+Na]$^+$.

Identification of On-Target and Off-Target Proteins of COMT Inhibitors by CCMS

Specific binders of tolcapone in a refined experimental setup were analyzed using so called differential competition experiments across a much larger set of replicate samples, dose-dependent CCMS experiments and improved analysis of mass spectrometric data. The focus of the study was on whole cell lysates from the human hepatocyte cell line HepG2. As reported earlier, catechol moieties are expected to target the COMT binding pocket, whereas the benzylic side of tolcapone protrudes outside the protein and points in the opposite direction to the catechol group.

Different parts of a drug may produce different interactions with cellular proteins inducing different responses. Therefore, two points of attachment for the tolcapone selectivity function to the Capture Compound scaffold were used in this study (CPT-224: active Tcp-CC and CPT-220: inactive Tcp-CC, FIG. 3). In the active orientation, the Capture Compound should be able to specifically interact with the known target COMT, in the other orientation, there could still be interactions with some off-target proteins.

To test the activities of Capture Compounds against COMT, the COMT inhibition assays against in-house expressed recombinant human COMT protein were performed.

As expected, the Capture Compound with the opposite orientation (CPT-220) in which tolcapone was linked via the catechol moiety had no affinity to COMT. The Capture Compound (CPT-224) attached via the benzylic moiety of tolcapone, leaving the nitrocatechol moiety free to interact with the target, displayed an IC$_{50}$ of 648 nM to the recombinant human COMT, corresponding to a ~10 fold reduction of activity compared to the parent molecule.

The protein interaction profile of small COMT inhibitors were investigated by performing CCMS experiments in the hepatoma-derived cell line HepG2. Enrichment and isolation of specifically interacting proteins were carried out using the inactive Capture Compound (CPT-220) and active Capture Compound (CPT-224) at a concentration of 1 μM. In the differential competition control experiments, an excess of the respective free small COMT inhibitors (tolcapone, entacapone, CPT-401 (A1) and CPT-212 (B1)) were added to compete with the Capture Compound for specific binders at 50 μM end concentration. The captured and trypsinized proteins were identified using a high resolution LTQ Orbitrap hybrid mass spectrometer. Only proteins identified with more than 99% probability and at least two unique peptides with 95% probability were considered to be identified with sufficient confidence. In competition control experiments, an excess of the respective free drugs was added that compete with the corresponding CC for specific binding sites.

As expected, no COMT was identified with the inactive Capture Compound (CPT-220), three proteins fulfilled our criteria and were competed by all the four different competitors, these proteins are Pyridoxal kinase (PDXK), Aldo-keto reductase family 1 member B10 (AKR1B10) and Protein NipSnap homolog 3A (NIPSNAP3A) (Table 1). When the active Capture Compound (CPT-224) was applied, COMT was the most robustly identified protein, along with other three proteins (Kynurenine-oxoglutarate transaminase 3 (CCBL2), 1,2-dihydroxy-3-keto-5-methylthiopentene dioxygenase (ADI1) and Glutaryl-CoA dehydrogenase (GCDH), Table 1) which fulfilled the inventors' criteria and were competed by all the four different competitors.

The main interest is in the proteins which show different competition specificities when the active tolcapone Capture Compound was used, and this so called differential competition dCCMS enabled the identification of the potential off-target causing toxicity of this small molecule COMT inhibitor. In the experiments, the protein HIBCH shows a unique capture pattern when the inventors compared specifically identified proteins using the four competitors. HIBCH was specifically identified when tolcapone was used as competitor, while no competition was observed in the presence of entacapone. Interestingly, HIBCH was specifically competed when CPT-212 (B1) was used as the competitor, and no competition was observed when CPT-401 (A1) was used. FIG. 5A shows the capture pattern of HIBCH intensities using the four different COMT inhibitors.

again captured only with Capture Compound in active orientation except for a weak unspecific interaction at the highest concentration of CPT-220 (5 μM), complete competition was observed with both competitors (tolcapone and CPT-401 (A1)). The same was observed for HIBCH protein in terms of the different orientations, HIBCH was not identified in the inactive orientation of tolcapone-CC (CPT-220). In contrast HIBCH was competed only with tolcapone-CC (CPT-224) in the active orientation but not with CPT-401 (A1). The clear dose-dependency and the consistent competition pattern of the binding intensities in this experiment further strengthens the validity of the dCCMS assay.

A unique feature of Capture Compounds is the formation of a covalent bond between the Capture Compound and the target protein, and the engagement of the target protein was competed in the presence of the small molecules which bind to the same binding pocket of the target proteins. The inventors carried out capture assays in HepG2 lysate followed by anti-HIBCH and anti-COMT Western Blots to investigate the binding profiles of the different competitors towards these proteins by a mass spectrometry-independent readout method. FIG. 6A shows that HIBCH was captured by CPT-224, and capturing was abolished when tolcapone or CPT-212 (B1) were used as competitor, but not with entacapone or CPT-401 (A1). In addition, the direct cross-link of CPT-224 to HIBCH was confirmed by streptavidin Western Blot (FIG. 6B) that detects biotinylation of the target protein after cross-link of the CC. The same experiment was performed using COMT Western Blot (FIG. 6C). Binding to COMT was only observed in the assay using active capture compound, and signals were abolished when any of the four small molecules tolcapone, entacapone, CPT-401 (A1) and CPT-212 (B1) were used as competitors, and also the biotinylation of COMT was abolished in the presence of the four competitors (FIG. 6D). This observation correlates very well with the Mass Spectrometry dataset (FIGS. 5A and 5B),

TABLE 1

Proteins significantly enriched by CCMS experiments using active capture compound (upper 4 panels) and inactive tolcapone capture compound (lower 3 panels) and competed by all four COMT inhibitors.

| Protein | Uniprot ID | Full name | MW [KDa] | Assay MS/MS | CPT-401 MS/MS | Fc | p-value | CPT-212 MS/MS | Fc | p-value |
|---|---|---|---|---|---|---|---|---|---|---|
| ADI1 | Q9BV57 | 1,2-dihydroxy-3-keto-5-methylthiopentene dioxygenase | 21 | 4.3 | 0.3 | 3.67 | 4.8E−5 | 0.3 | 4.29 | 3.9E−4 |
| CCBL2 | Q6YP21 | Kynurenine-oxoglutarate transaminase 3 | 51 | 7.3 | 2.6 | 3.05 | 3.0E−4 | 2 | 3.40 | 3.1E−4 |
| COMT | P21964 | Catechol O-methyltransferase | 30 | 18 | 3 | 34.2 | 3.0E−5 | 5 | 10.90 | 4.1E−5 |
| GCDH | Q92947 | Glutaryl-CoA dehydrogenase | 48 | 7.6 | 2.6 | 5.90 | 2.0E−4 | 2.3 | 6.34 | 1.8E−4 |
| PDXK | O00764 | Pyridoxal kinase | 35 | 3.25 | 0 | 16 | 0.001 | 3.75 | 24.9 | 0.0009 |
| AKR1B10 | O60218 | Aldo-keto reductase family 1 member B10 | 36 | 6.5 | 0.5 | 4.7 | 0.007 | 0 | 3.1 | 0.015 |
| NIPSNAP3A | Q9UFN0 | Protein NipSnap homolog 3A | 28 | 1.25 | 0 | 7.5 | 0.001 | 0.025 | 3 | 0.018 |

Verification of Small Molecule Binding to HIBCH

In order to further investigate the binding of tolcapone to HIBCH, dose-dependent capturing was performed. The results from dose-dependent capture experiments using CPT-220 or CPT-224 at different concentrations from 5 μM to 40 nM and tolcapone or CPT-401 (A1) as competitor are shown in FIG. 5B. As expected, the COMT protein was which confirms that tolcapone, entacapone, CPT-401 (A1) and CPT-212 (B1) are all potent COMT inhibitors and the binding of CPT-212 (B1) to HIBCH might take place in the same binding pocket as binding of tolcapone to HIBCH.

To verify this hypothesis, docking experiments for all four small molecules to COMT and HIBCH were conducted. The two novel COMT inhibitors, CPT-212 (B1) and CPT-401

(A1) fit to the binding pocket (active site) of COMT. In contrast, only bent structures like tolcapone and CPT-212 (B1) can "dive" deep into the proposed small molecule binding pocket of HIBCH with the catechol interacting with the catalytic glutamine acid side chain, while entacapone and CPT-401 (A1) do not, even if the docking was restrained with respect to the position of the catechol moiety. This can be explained by common structural features of the two molecule pairs: tolcapone and CPT-212 (B1) adopt a conformation where the two aromatic moieties are tilted against each other which neatly fit into the HIBCH small molecule binding pocket. But the other two inhibitors entacapone and CPT-401 (A1) prefer or are even restricted to obtain an overall planar conformation.

Cytotoxicity Results of the COMT Inhibitors

In previous publications, the inventors reported that the cellular distribution of protein binders of entacapone show no link to mitochondrial function, but large proportions of protein binders of tolcapone are of mitochondrial origin, especially mitochondrial membrane (Fischer, Toxicol Sci, 2010. 113(1): 243-53). In order to evaluate the possible mitochondrial toxicity of the novel COMT inhibitors in a cell-based assay, the Mitochondrial ToxGlo™ assay was conducted, in which HepG2 cells were grown in galactose-containing or glucose-containing media to detect mitochondrial toxicity on the basis of measuring the ATP content of the cells. A decrease in ATP output is only associated with growth in galactose-containing medium and thus probably a result of mitochondrial dysfunction. Besides tolcapone and entacapone, the two new small molecule COMT inhibitors, CPT-401 (A1) and CPT-212 (B1), were included in the analysis. As reported above, they are potent COMT binders but differ in terms of their off-target profiles. The profile of CPT-212 (B1) resembled the profile of tolcapone, and the CPT-401 (A1) resembled the profile of entacapone.

The results from this assay (FIG. 7) show that for tolcapone, there is more than a 4 fold lower $IC_{50}$ value observed in the galactose media compared to the glucose media, which indicates that tolcapone is a mitochondrial toxicant. In contrast, a much smaller effect was observed for entacapone. These results further support the findings of a previous study carried out by the inventors which revealed the mitochondrial localization of tolcapone target proteins. Interestingly, when the mitochondrial toxicity of CPT-401 (A1) and CPT-212 (B1) was compared, the changes in $IC_{50}$ values for the galactose and glucose media for CPT-401 (A1) were much less than for CPT-212 (B1), which indicates that the mitochondrial toxicity of CPT-401 (A1) is less than for CPT-212 (B1).

Overexpression of COMT and HIBCH

A His-S-COMT expression vector was purchased from Origene (NM_007310) and for the cloning of HIBCH, RNA was isolated from HepG2 cells using RNeasy Mini Kit (Qiagen) wherefrom cDNA was synthesized using SuperScript III Reverse Transcriptase (Invitrogen). Using the HepG2 cDNA as a template, PCR reactions were run with the following primers: 5'-gatcgaattcatggggcagcgcgagatg-3' (HIBCH forward), 5'-gatcctcgagtcaaaatttcaaatcactgcttcc-caaa-3' (HIBCH reverse), inserting EcoRI and XhoI restriction sites. A G3PDH PCR reaction with the following primers: 5'-tgaaggtcggagtcaacggatttggt-3' (G3PDH forward) and 5'-catgtgggccatgaggtccaccac-3' (G3PDH reverse) were run in parallel as control. PCR and restriction products were purified using the peqGOLD Gel Extraction Kit (peqlab). Restriction of PCR fragments and target vector (pET28a+, Merck Millipore) was performed at 37° C. for 2 hours in the presence of FastDigest restriction enzymes and FastDigest Green Buffer (Thermo Scientific). After 1 h 40 min, CIP enzyme was added to the vector reaction which was incubated at 37° C. for another 20 min. Ligation reactions were incubated at 16° C. over night using T4 DNA Ligase (Roche). 500 ng DNA construct with S-COMT and HIBCH was used for transformation of competent BL21 E. coli cells and expression of recombinant proteins were induced by IPTG. The cells were collected by centrifugation (15 min, 4000 g, 4° C.). Cells were re-suspended in 5 ml of buffer (COMT: 50 mM phosphate, 300 mM NaCl, 5 mM $MgCl_2$, pH 7.4, HIBCH: 20 mM Tris, 500 mM NaCl, 10 mM imidazole, 0.5% (w/v) Triton X-100, pH 8.0) and disrupted by treatment with lysozyme and DNase I followed by sonication. The supernatant from the subsequent centrifugation (the cytosolic fraction) was used as protein source in subsequent experiments.

COMT Activity Microplate Assay

COMT activity measurement experiments were essentially performed as described previously (Kurkela, Anal Biochem, 2004. 331(1): 198-200). In short, aesculetin (Sigma-Aldrich) and competing catechol substrates were dissolved in dimethyl sulfoxide (DMSO) and diluted with aqueous buffer solution (100 mM phosphate, 5 mM $MgCl_2$, 20 mM L-cysteine, pH 7.4) for a final DMSO concentration of 2% in 100 µl of reaction mixture. All of the reagents were dissolved in the same buffer solution. For each sample, inhibitor and aesculetin solutions were pipetted in triplicates into a black round-bottomed 96-well plate. Controls without inhibitor or AdoMet were included in each microplate. The plate was placed on ice, and the cytosolic fraction containing the enzyme was added to a final protein concentration of 15 µg/ml. A pre-incubation period of 5 min was started by placing the microplate at 37° C. and the reaction was initiated by addition of AdoMet, at 37° C., for a final concentration of 10 µM. Fluorescence was measured at the start of the reaction and at 60 min using a CARY Eclipse Fluorescence Spectrophotometer. The excitation and emission wavelengths were 355 nm and 460 nm, respectively. Enzymatic activity was estimated by subtraction of fluorescence at the beginning of the assay from the fluorescence at 60 min and inhibition curves were generated using GraphPad Prism.

Capture Experiments

Capture experiments were carried out with 500 µg of HepG2 lysate (InVivo, Germany) or 1 µg of human recombinant COMT or 1 µg human recombinant HIBCH protein, supplemented with 5 µM AdoMet (Sigma-Aldrich), 20 µl of 5× capture buffer (caprotec bioanalytics GmbH) and incubated with DMSO or 50 µM competitor in a total volume of 100 µl at 4° C. for 30 min. After incubation with Capture Compound at 4° C. for 1 h, samples were irradiated for 10 min using the caproBox (Caprotec Bioanalytics GmbH). Subsequently, buffer conditions were adjusted by adding 25 µL of 5× wash buffer (WB, caprotec bioanalytics GmbH, Berlin, Germany) to each reaction. The samples were then incubated with 50 µL Dynabeads MyOne Streptavidin C1, (Invitrogen, Karlsruhe, Germany) for 1 h at 4° C. on a rotation wheel. The beads containing the CC-protein conjugates were then collected using the caproMag, a device for the convenient and efficient isolation of biomolecules when using magnetic beads (caprotec bioanalytics GmbH, Berlin, Germany), and washed first six times with 200 µL 1×WB, then with MS grade water. The beads were stored at 4° C. in deionized water until further analysis by either SDS-PAGE or protein digestion followed by LC-MS.

Protein Digest and Mass Spectrometric Analysis

After protein capturing, streptavidin magnetic beads were washed twice with 200 µL of LC-MS grade water (Fluka, St. Louis, Mo., USA). For tryptic digestion, the proteins bound to the streptavidin magnetic beads were incubated with 9 µL of 50 mM ammonium bicarbonate and 1 µL of trypsin (0.5 µg/µL) (Roche, Germany) for 16 h at 37° C. on a temperature-controlled shaker. The supernatant was removed and evaporated to dryness in a miVac DNA vacuum centrifuge (Genevac, UK) and used directly for mass spectrometric analysis. The tryptic digests were analyzed by online nano-litre liquid chromatography tandem mass spectrometry (nl LC-MS/MS) on an UltiMate 3000 RSLCnano System coupled to a LTQ-Orbitrap Velos instrument (Thermo Fisher Scientific, Germany) through a Proxeon nano-electrospray ion source (Thermo Fisher Scientific, Germany). For chromatographic separation, samples were first loaded on a reversed phase (RP) precolumn (Acclaim PepMap100) and separated on a RP analytical column (Acclaim PepMap RSLC C18, Dionex, Thermo Fisher Scientific, Germany). Mass spectrometric analysis was performed in the data-dependent mode allowing automatic switching between Orbitrap-MS and LTQ-MS/MS acquisition for a full scan with subsequent collision-induced dissociation (CID) fragmentation. Full scan MS spectra (from m/z 300-2000) were acquired in the Orbitrap analyzer. The 20 most intense ions were sequentially isolated and fragmented in the linear ion trap using CID.

All MS/MS data were analyzed using search engine Andromeda implemented in MaxQuant (www.maxquant.org, release 1.4.0.8). Automated database searching against the human UniProtKB/Swiss-Prot database (release 2015_02 contains 20203 reviewed sequence entries) was performed with 6 ppm precursor tolerance, 0.5 Da fragment ion tolerance, full trypsin specificity allowing for up to 2 missed cleavages and methionine oxidation as variable modification. The maximum false discovery rates were set to 0.01 both on protein and peptide level and 6 amino acids were required as minimum peptide length. The label-free quantification option was selected for alignment between LC-MS/MS runs. The output of the MaxQuant analysis was post-processed according to a standardized procedure implemented at caprotec bioanalytics GmbH to normalize protein intensities, and subsequently calculate fold changes and p-values.

Therefore, proteins that are detected by LC-MS in the capture assay and that are significantly diminished in competition control experiments are defined to be specific. The specificity was quantified by the fold change between assay and competition for each protein. Moreover, experiments were carried out in quadruplicate, allowing the determination of significance by calculating of p-values.

ATPlite Cytotoxicity Assay

Mitochondrial toxicity assessment (Glu/Gal) of the compounds tolcapone, entacapone, CPT-401 (A1) and CPT-212 (B1) was conducted by Pharmacelcus GmbH. Briefly, HepG2 cells cultured in glucose media (high glucose DMEM containing 22 mM glucose, 1 mM sodium pyruvate, 5 mM Hepes, 2 mM L-glutamine, 10% FCS, and 1% penicillin/streptomycin) or galactose media (high glucose DMEM containing 10 mM galactose, 1 mM sodium pyruvate, 5 mM Hepes, 2 mM L-glutamine, 10% FCS, and 1% penicillin/streptomycin) were added to a 96 well plate (100 µL, 4×104 cells/well). For drug treatments, compound stock solutions were prepared in DMSO and added into the wells to give the indicated final drug concentrations. The final DMSO concentration in each well after the addition of luminescent ATP detection reagent was 0.5%. A total of 100 µL of the luminescent ATPlite (PerkinElmer) detection reagent was added to each well. After a brief mix on a plate shaker, the reactions were incubated at room temperature for 2 min, and luminescence was measured after 2 min using a Victor X5 plate reader.

TMRE Mitochondria Membrane Potential Assay

For the TMRE mitochondria membrane potential assay, HepG2 cells were treated with four COMT inhibitors at different concentrations. TMRE (tetramethylrhodamine ethyl ester), a cell permeable, positively charged, red-orange dye that readily accumulates in active mitochondria due to their relative negative charge, was used to label active mitochondria. Significant difference in mitochondrial membrane potential status between the four COMT inhibitors was observed (FIG. 9). At a concentration of 50 µM, the compounds tolcapone and CPT212 suppressed the membrane potential to less than 20-30% of untreated HepG2 cells, while more than 50% of the membrane potential was still observed using the compounds entacapone or CPT401. CPT212 and tolcapone at a concentration of 100 µM, reduced the membrane potential to 0-5% of the control, while for CPT401 and entacapone, 40-50% of the membrane potential remained at this concentration. The data demonstrate a close resemblance between entacapone and CPT401, as well as between tolcapone and CPT212 in terms of the mitochondria membrane potential at concentrations between 10 and 100 µM. The mitochondrial membrane potential (MMP) was measured using the positively charged fluorescent dye TMRE, which readily accumulates in active mitochondria. FCCP, an ionophore uncoupler of oxidative phosphorylation, served as the positive control. HepG2 cells were seeded into pClear bottomed, black 96-well plates (ca. 4×104 cells/well). After reaching confluency, the cells were treated with four COMT inhibitors (tolcapone, entacapone, CPT401, or 3) at individual defined final concentrations overnight at 37° C. and 5% CO2. The culture media were removed and replaced with fresh media, TMRE was added to the media at 200 nM final concentration, and cells were incubated for 30 min at 37° C. and 5% CO2. After incubation, cells were washed with PBS with 0.2% BSA, and the fluorescence intensity was measured using a Cary Eclipse fluorescence microplate reader equipped with at 549 and 575 nm excitation and emission filters, respectively.

Computational Methods

All used software tools are in included in the SYBYL×1.2 package (Tripos Inc. St. Louis, Mo.). For the preparation of molecular structures, atomic coordinates of human beta-hydroxyisobutyryl-CoA hydrolase (HIBCH_HUMAN) in complex with quercetin (QUE) and (2R)-3-hydroxy-2-methylpropanoic acid (HIU) was obtained from the PDB file 3BUT. The structure was preprocessed using the Prepare Protein tool and minimized using the MMFF force field, MMFF charges and the Powell gradient algorithm (rmsd 0.5). All heavy atoms were frozen during minimization. QUE was removed to get access to the catalytic site. Ligand structures were obtained from 2d sketches (ChemDraw) using the Ligand Tool: The structures were standardized, and tautomers were generated (count of charged atoms=4). Catechol dianions were removed with the substructure SMARTS filter (O[-1]C:CO[-1]) and one 3D structure per tautomer was generated using Concord Standalone. Atom types on the catechols and nitro groups were set as follows: O-→O.co2; N→N.pl3, using an SPL script. The resulting structures were minimized using the default settings (Tripos FF, rmsd=0.05) and Gasteiger-Marsili charges. Unrestrained flexible docking between HIBCH and the putative inhibitors tolcapone, entacapone, CPT-212 (B1), and CPT-401 (A1) was performed with Surflex-Dock. The co-crystallized product HIU was extracted and the protocol was generated based on HIU. Protein flexibility (Hydrogens and heavy atoms) was allowed and 10 start conformations generated. Otherwise, default settings were used. 100 poses were sampled and investigated with respect to the docking scores, catechol position, and protein. The best docking pose of tolcapone was used as basis for a catechol fragment. The docking was repeated using weakly restricted fragment placing (cpen=10).

Abbreviations

CAN, Ceric Ammonium Nitrate; CC, Capture Compound; CCMS, Capture Compound mass spectrometry; dCCMS, differential competition Capture Compound mass spectrometry; DCM, Dichloromethane; DIPEA, N,N-Diisopropylethylamine; DMF, N,N-Dimethylformamide; DMSO, Dimethyl sulfoxide; HATU, O-(7-Azabenzotriazol-1-yl)-N,N,N',N'-tetramethyluronium hexafluoro-phosphate; TEA, Triethylamine; THF, Tetrahydrofuran.

Figure 1:
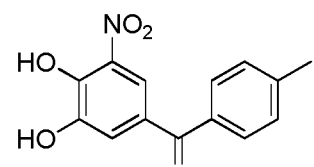
FIG. 1 shows the chemical structures of tolcapone, entacapone and the two lead COMT inhibitors CPT-401 (A1) and CPT-212 (B1).
Figure 1:
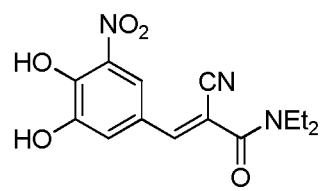
Figure 1:
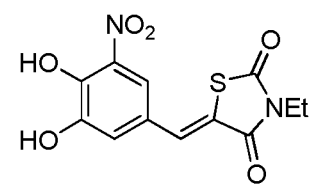
Figure 1:
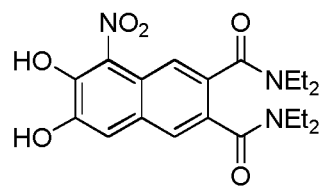
Figure 2:
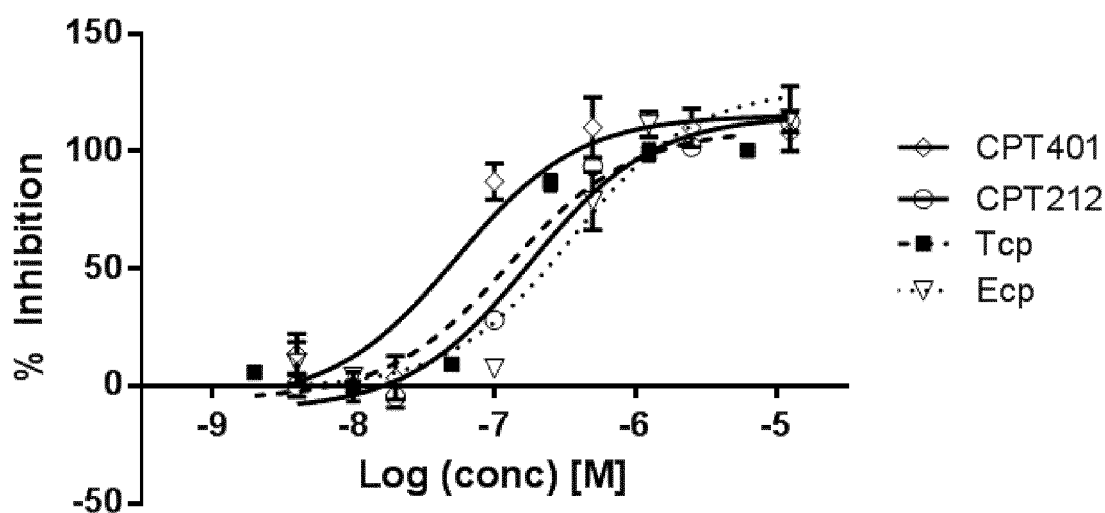
FIG. 2 shows the inhibition of human recombinant COMT by tolcapone, entacapone, CPT-401 (A1) and CPT-212 (B1).
Figure 3:
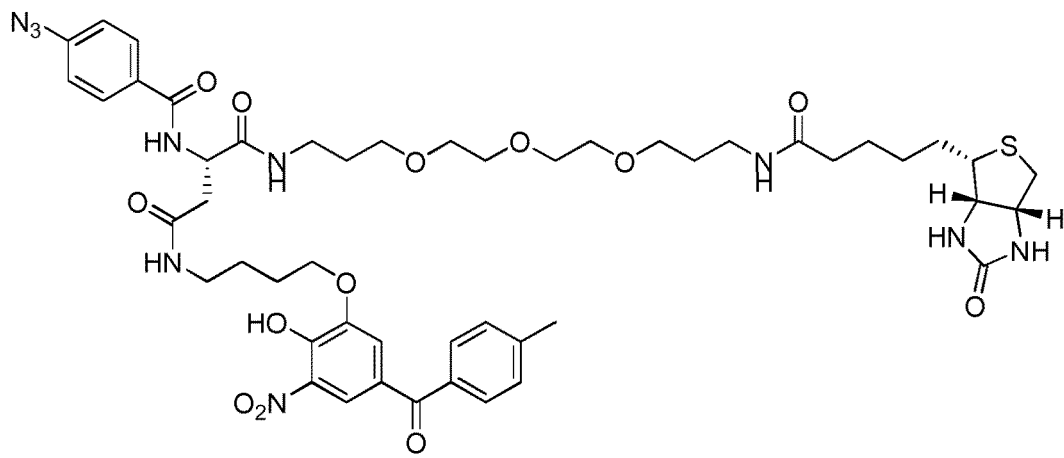
FIG. 3 shows the chemical structures of tolcapone capture compounds in inactive (attachment via the catechol function, CPT-220) and active (attachment via benzylic group with free catechol function, CPT-224) orientation.
Figure 3:
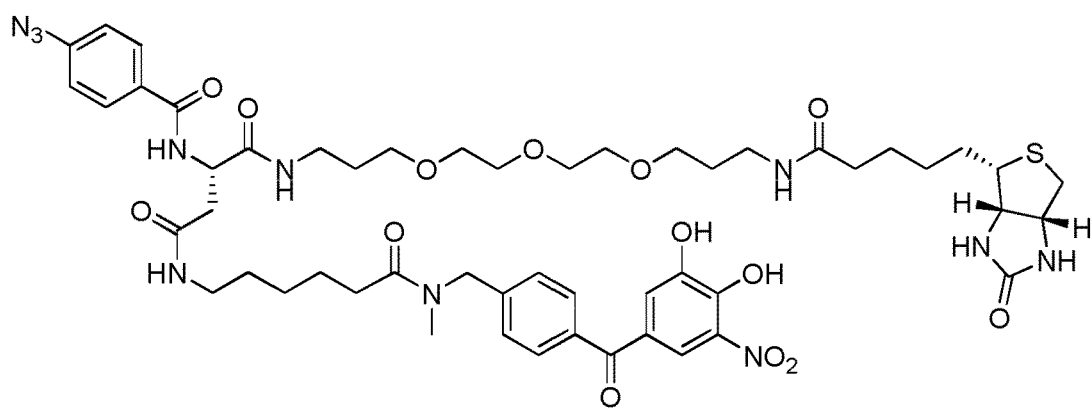
Figure 4:
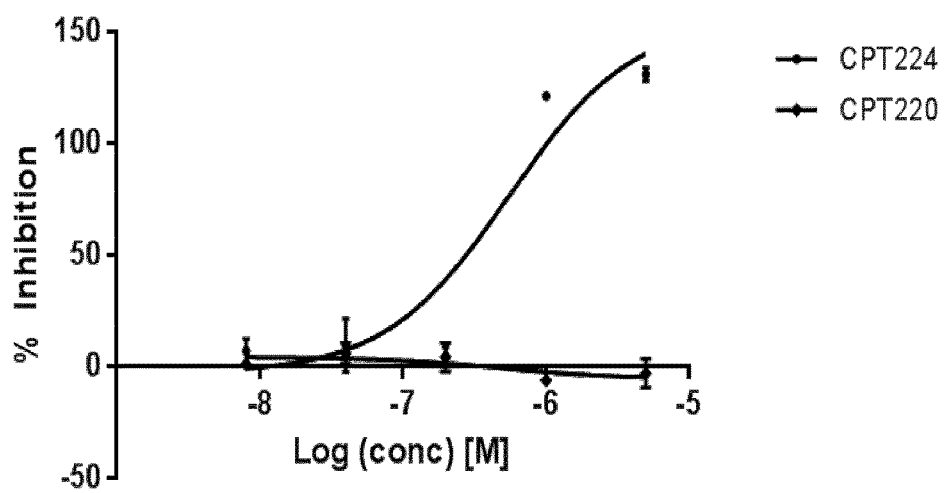
FIG. 4 shows the inhibition of human recombinant COMT by active tolcapone capture compound (CPT-224) and inactive tolcapone capture compound (CPT-220).
Figure 5A:
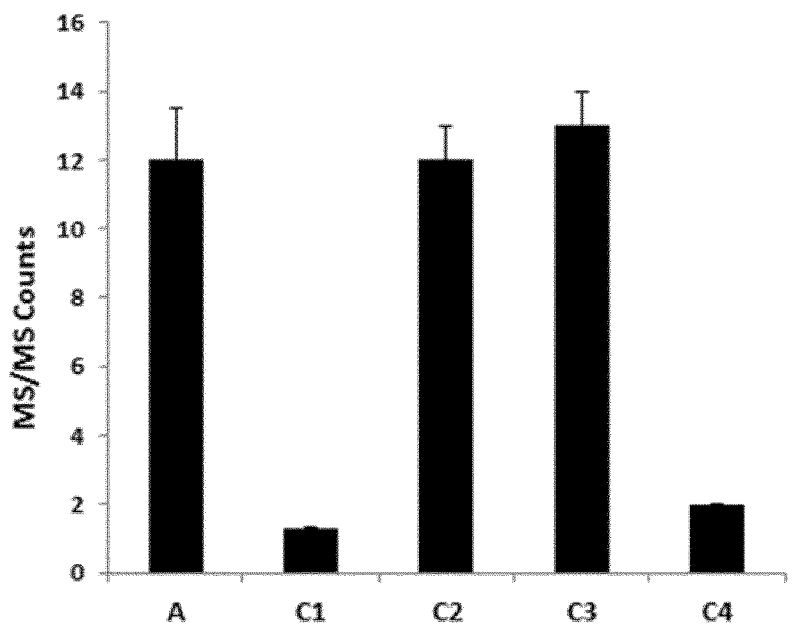
FIG. 5A shows the results of differential competition Capture Compound Mass Spectrometry experiments comprising the average MS/MS and the normalized intensities of HIBCH identified in the dCCMS experiments: A: Assay; C1: tolcapone as the competitor; C2: entacapone as the competitor; C3: CPT-401 (A1) as the competitor; C4: CPT-212 (B1) as the competitor. Data are mean plus SD (n=4). The table gives the FC and p-value of the HIBCH protein in the capturing experiments using CPT-224 with different competitors (C1: tolcapone, C2: entacapone, C3: CPT-401 (A1), C4: CPT-212 (B1)).
Figure 5A:
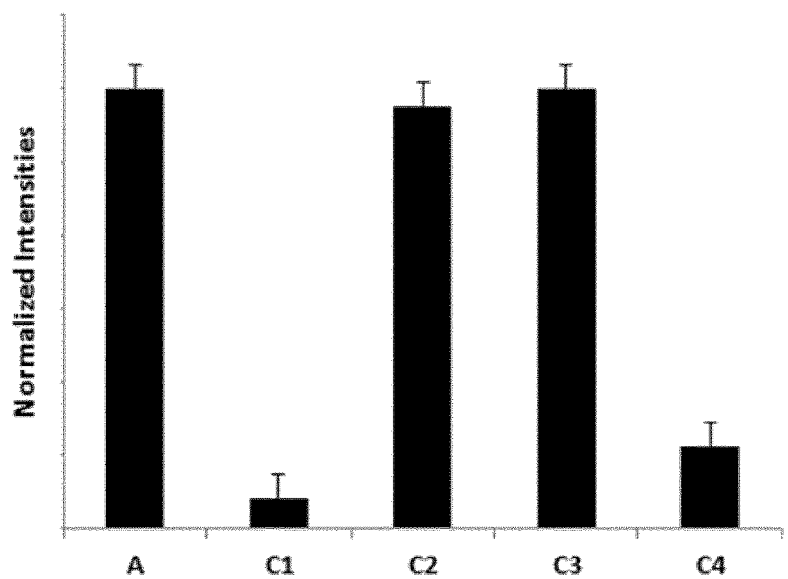
Figure 5B:
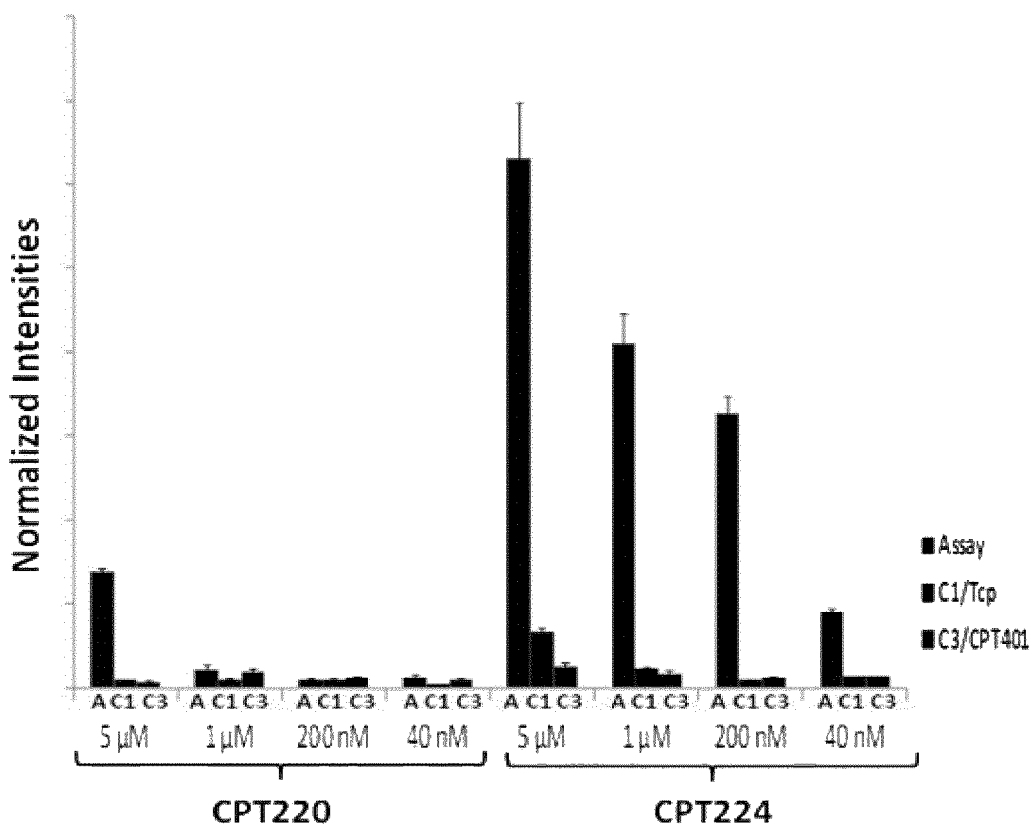
FIG. 5B shows dose-dependent capturing experiments using CPT-220 or CPT-224 at different concentrations from 5 μM to 40 nM. Left panel: CCMS results for the COMT protein; right panel: CCMS results for the HIBCH protein; Assay: Assay with CPT-220 or CPT-224; C1/Tcp: tolcapone as competitor in the presence of CPT-220 or CPT-224; C3/CPT-401: CPT-401 (A1) as competitor. Data are mean plus SD (n=4).
Figure 5B:
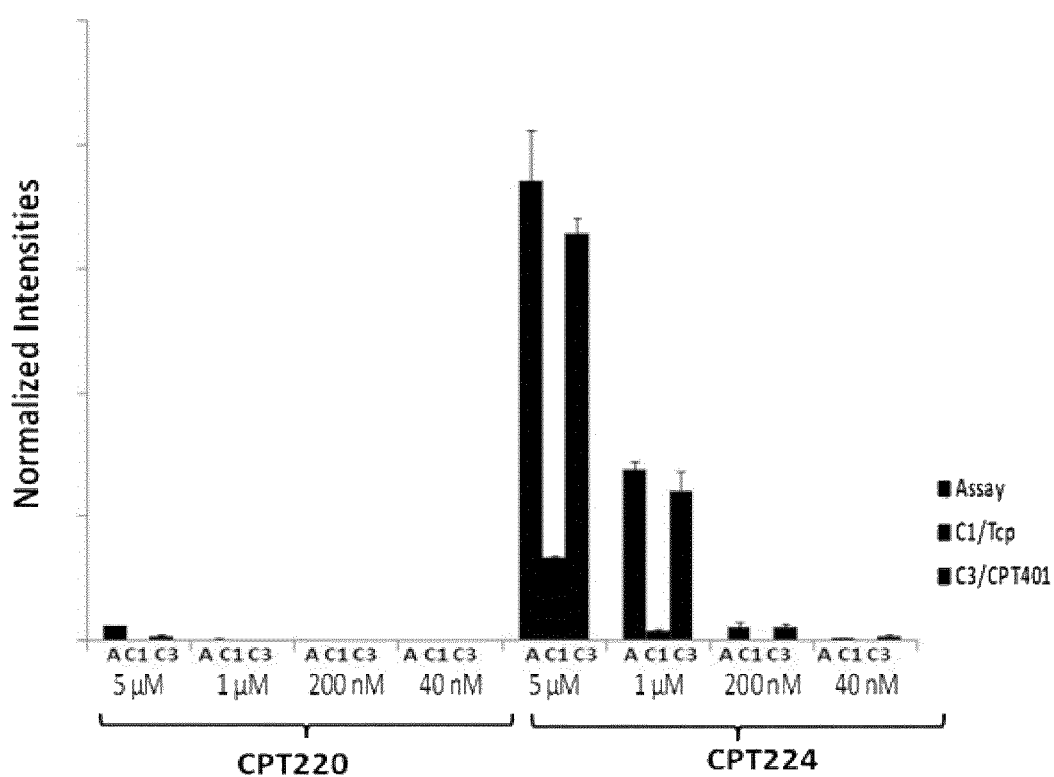
Figure 6:
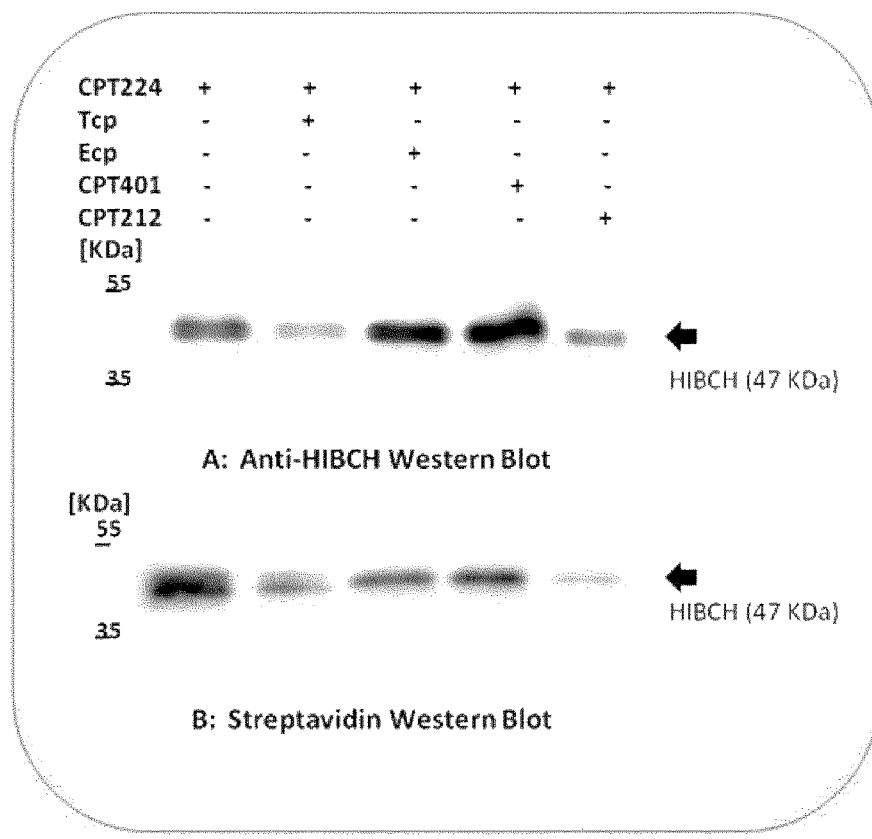
FIG. 6 shows the detection of COMT and HIBCH by Western Blot after differential competition Capture Compound crosslinking: Tcp-CC (CPT-224) captures recombinant HIBCH (left panel) and recombinant COMT (right panel) (A), Anti-HIBCH Western Blot demonstrates the identification of HIBCH protein. (B), anti-Streptavidine Western Blot demonstrates the crosslinking of HIBCH with CPT-224. The reaction was competed in the presence of Tcp and CPT-212 (B1), whereas no competition of HIBCH in the presence of Ecp and CPT-401 (A1) was observed. (C), anti-COMT Western Blot demonstrates the identification of COMT protein. D), Anti-Streptavidin Western Blot demonstrates the crosslinking of COMT with CPT-224. The reaction was competed in the presence of Tcp, Ecp, CPT-401 (A1) and CPT-212 (B1).
Figure 6:
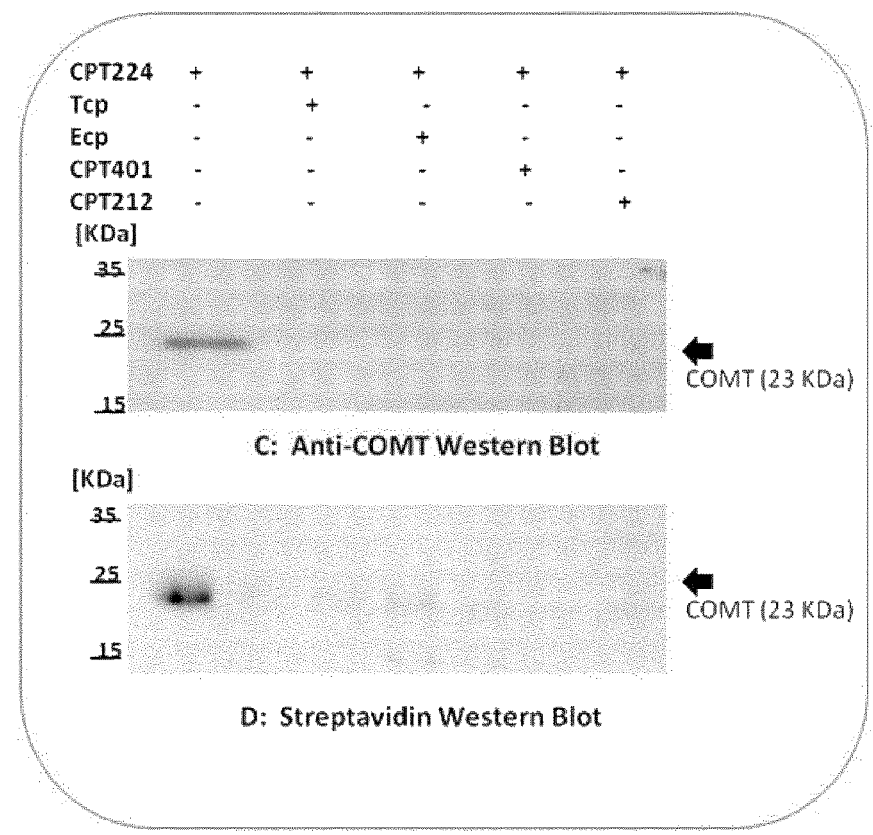
Figure 7:
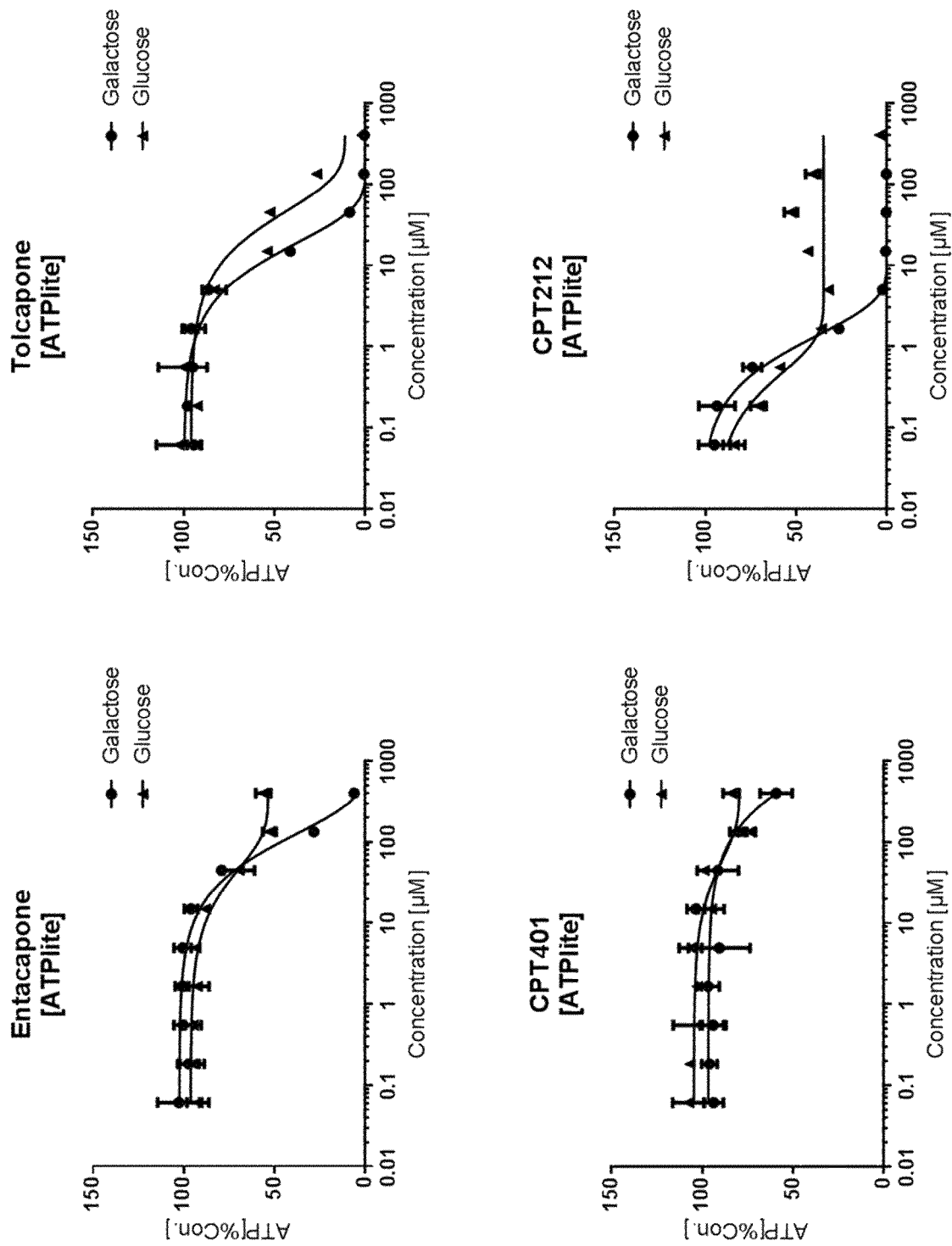
FIG. 7 shows the results of a cell-based mitochondrial toxicity assay using tolcapone, entacapone, CPT-401 (A1) and CPT-212 (B1). A decrease in ATP output associated with growth in galactose-containing medium is indicative of mitochondrial dysfunction. X-axis: ATP concentration; Y-axis: concentration of test compound.
Figure 8A:
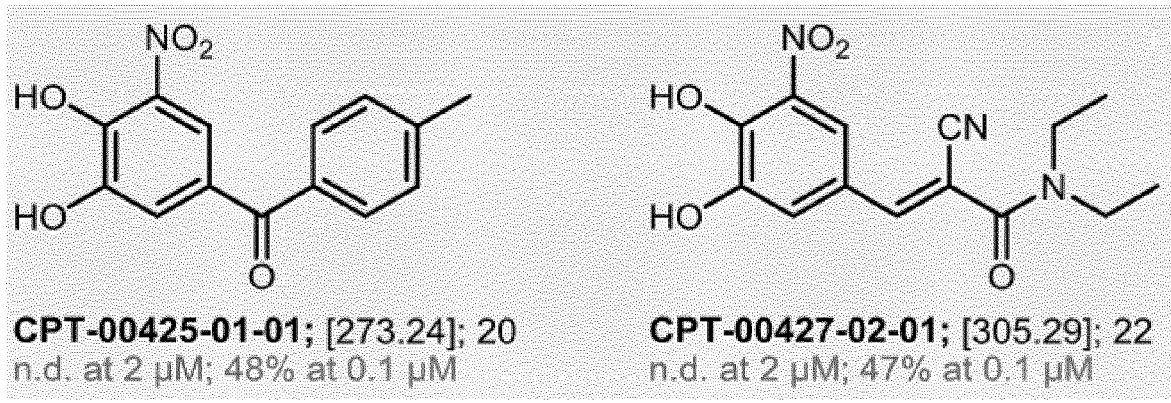
FIG. 8 shows the chemical structures of the COMT inhibitors and the results of a COMT inhibition assay at 2 μM and 0.1 μM concentrations. A: tolcapone, entacapone. B: derivatives of CPT-401 (A1). C: derivatives of CPT-212 (B1).
Figure 8B:
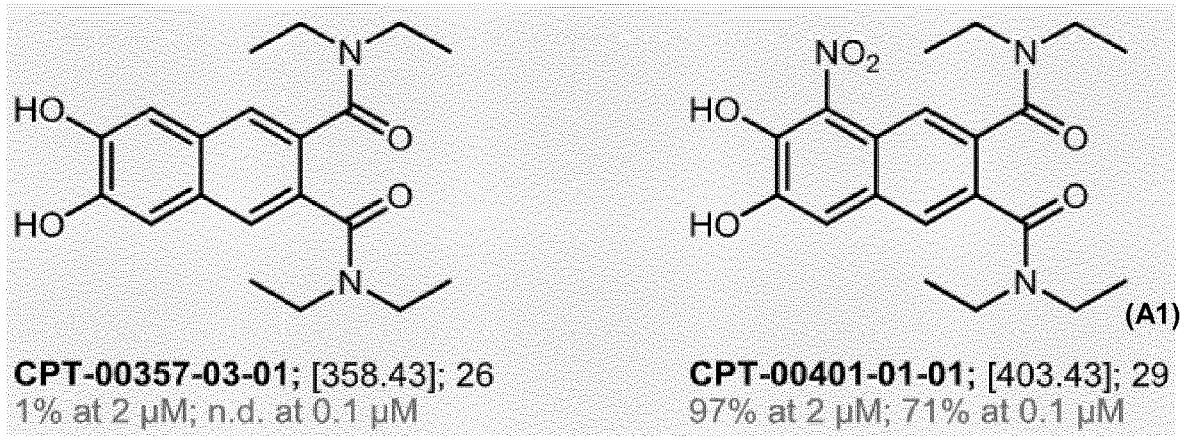
Figure 8C:
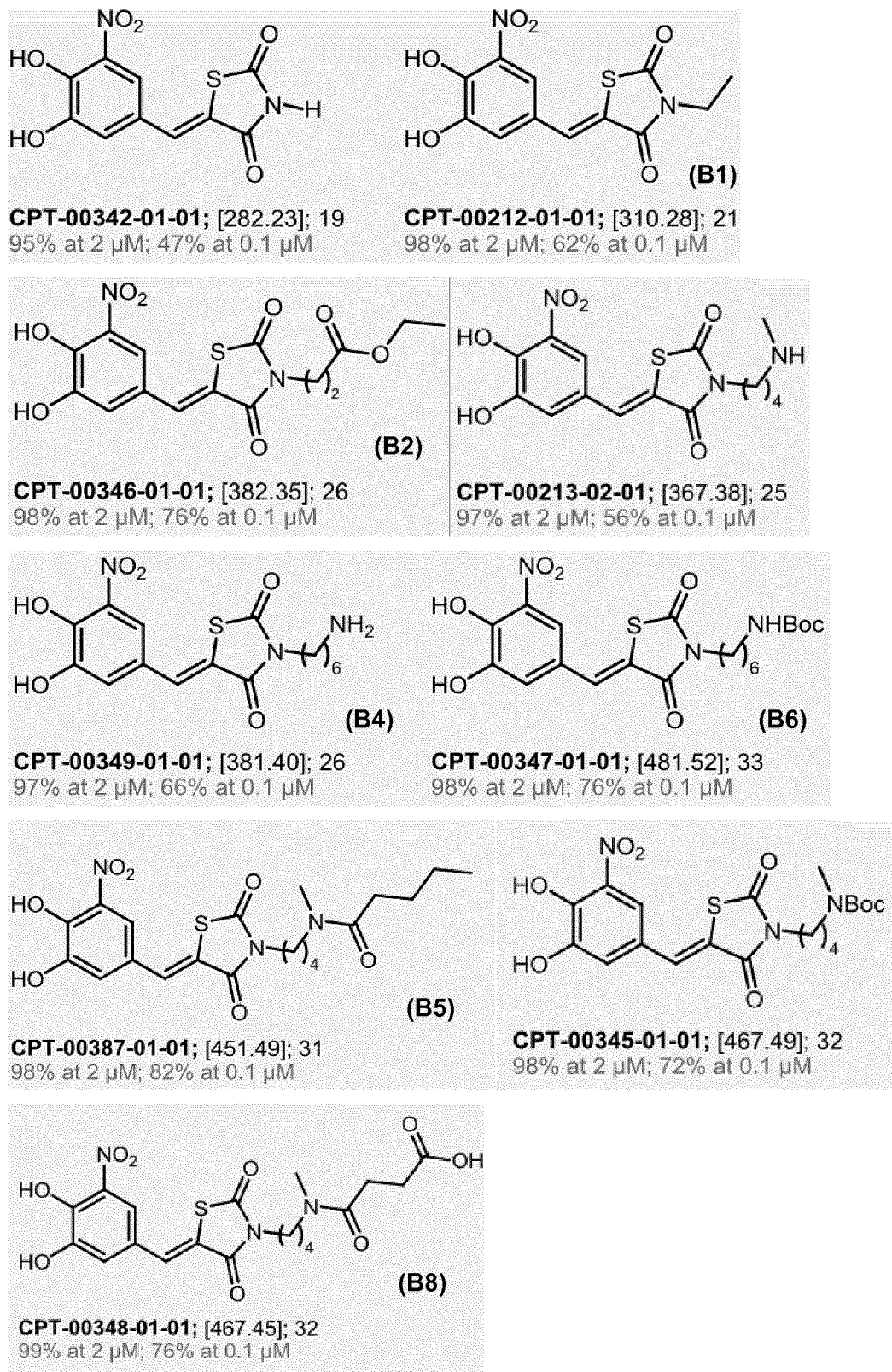
Figure 8:
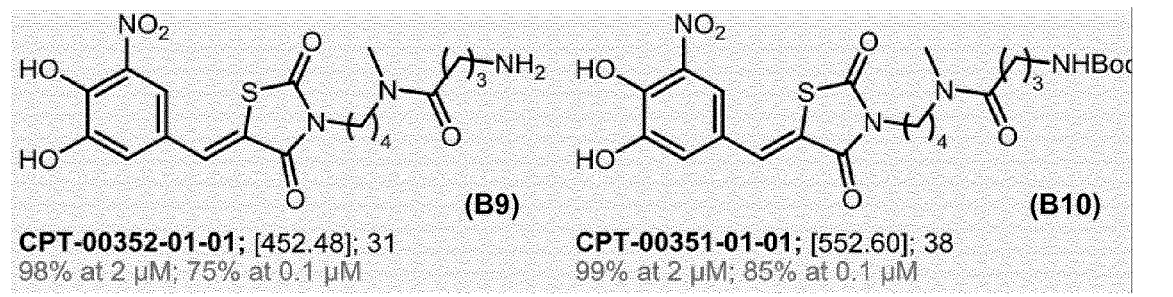
Figure 8:
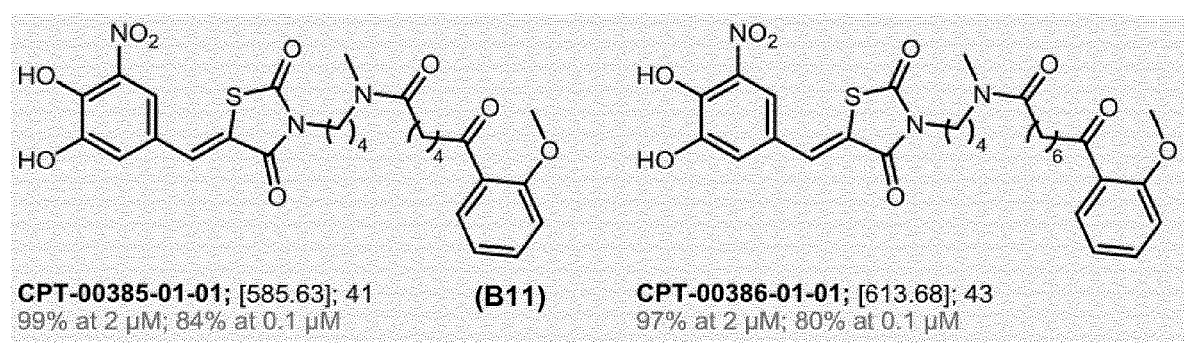
Figure 8:
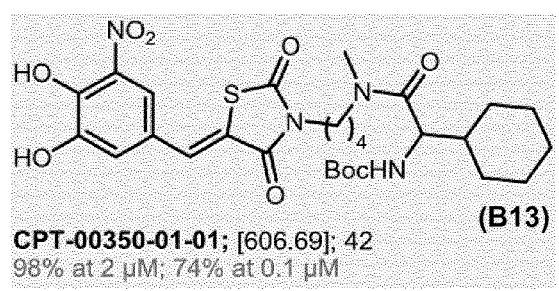
Figure 9:
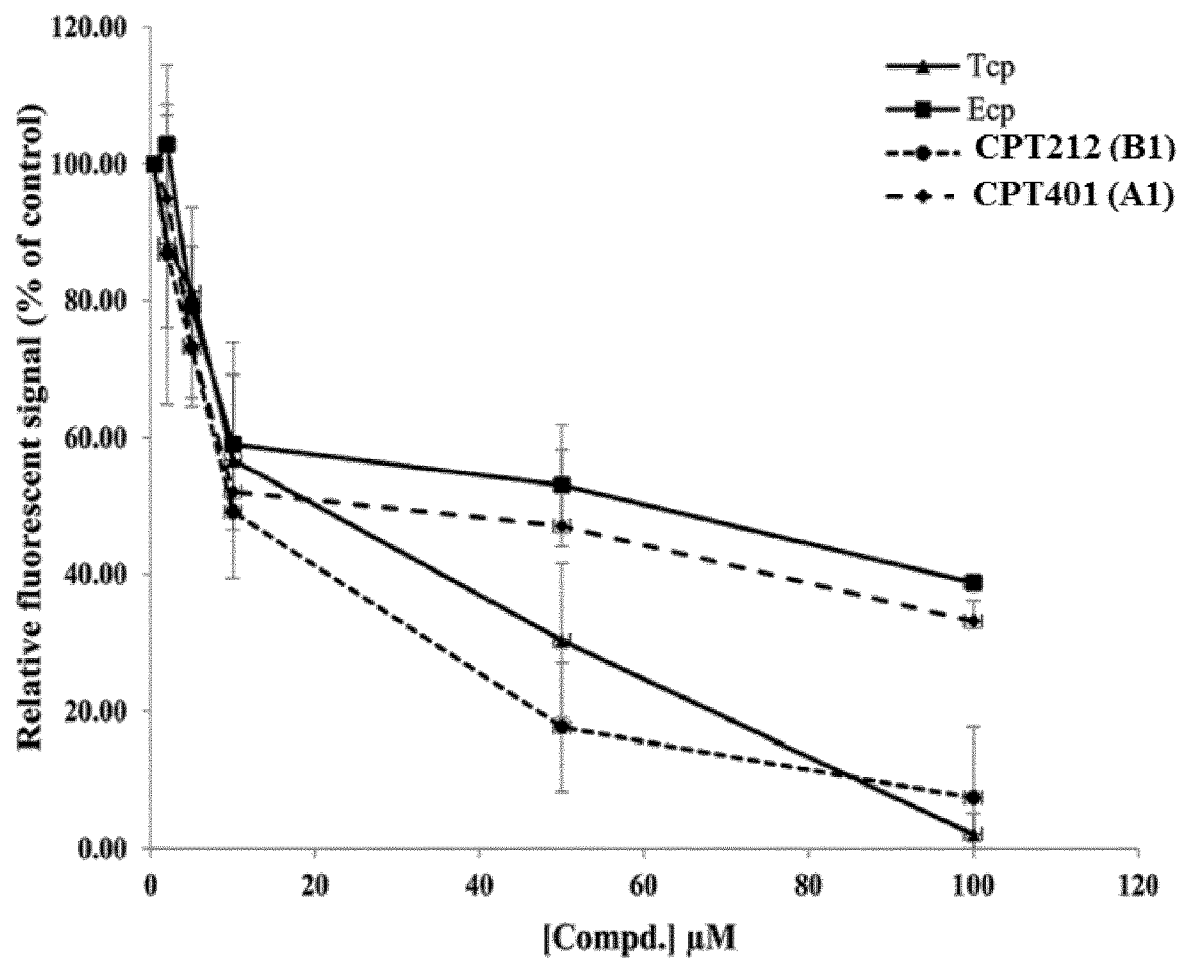
FIG. 9 shows the dose-dependent effect of tolcapone, entacapone, CPT-212 (B1), or CPT-401 (A1) on mitochondrial membrane potential (percentage of control) in HepG2 cells using the TMRE mitochondria membrane potential test. Data are the mean SD (n=6).

The invention claimed is:
1. A compound characterized by a general formula (A),

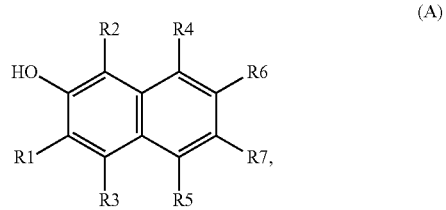

wherein
$R^1$ is selected from —OH, —SH and —NH$_2$;
$R^2$ is selected from —NO$_2$, —SO$_3$H, —SO$_2$—OR$^{11}$, —SO$_2$—NH$_2$, —SO$_2$—NHR$^{11}$, —SO$_2$—NR$^{11}$$_2$, —PO$_3$H, —PO$_2$—OR$^{11}$, —CN, —COR$^{11}$, —CO$_2$R$^{11}$, —CONHR$^{11}$, —CONR$^{11}$$_2$, —CF$_3$, and halogen;
$R^3$ is selected from H, —NO$_2$, —SO$_3$H, —SO$_2$—OR$^{11}$, —SO$_2$—NH$_2$, —SO$_2$—NHR$^{11}$, —SO$_2$—NR$^{11}$$_2$; —PO$_3$H, —PO$_2$—OR$^{11}$, —CN, —COR$^{11}$, —CO$_2$R$^{11}$, —CONHR$^{11}$, —CONR$^{11}$$_2$, —CF$_3$, and halogen;
$R^4$ and $R^5$ are independently selected from —H, substituted C$_1$-C$_6$ alkyl, unsubstituted C$_1$-C$_6$ alkyl, substituted or unsubstituted C$_2$-C$_6$ alkenyl, substituted or unsubstituted C$_3$-C$_6$ cycloalkyl, halogen, —CN and —NO$_2$;
$R^6$ and $R^7$ is selected from —CONH$_2$, —CONR$^9$$_2$ and —CONR$^{11}$R$^9$—, or
one of $R^6$ and $R^7$ is selected from —CONH$_2$, —CONR$^9$$_2$ and —CONR$^{11}$R$^9$, and the other one of $R^6$ and $R^7$ is H,
wherein
$R^9$ is R$^{10}$—(Y—R$^{10}$)$_n$
Y is selected from —CONR$^{11}$—, —CO—, —COO—, —SO$_3$—, —SO$_2$NH—, —NR$^{11}$—, —O—, —NR$^{11}$CO—, OCO—, —NR$^{11}$COO—, —NR$^{11}$CONR$^{11}$—, —OCONR$^{11}$— and —OCOO—
n is an integer selected from 0, 1, 2, 3 and 4,
each $R^{10}$ independently of any other $R^{10}$ is selected from a substituted or unsubstituted C$_1$-C$_8$ alkyl, substituted or unsubstituted a $C_2$-$C_8$ alkenyl, a substituted or unsubstituted $C_2$-$C_8$ alkynyl, substituted or unsubstituted a $C_3$-$C_{10}$ cycloalkyl and a substituted or unsubstituted 5- to 10-membered aryl or heteroaryl; and each $R^{11}$ independently of any other $R^{11}$ is H or an unsubstituted $C_1$-$C_6$ alkyl.

2. The compound according to claim 1, wherein $R^7$ is selected from —$CONR^{11}R^9$ and —$CONR^9{}_2$, with $R^9$ having the same meaning as defined above.

3. The compound according to claim 1, wherein
$R^1$ is —OH,
$R^2$ is —$NO_2$ and $R^3$ is H,
$R^4$ and $R^5$ are H,
$R^6$ is selected from H, —$CONH_2$, and —$CONR^9{}_2$,
$R^7$ is selected from —$CONR^9{}_2$ and —$CONR^{11}R^9$,
wherein $R^9$ and $R^{11}$ have the same meaning as defined above.

4. The compound according to claim 1, wherein n is 0.
5. The compound according to claim 1, wherein n is 1.
6. The compound according to claim 1, wherein n is 2.
7. The compound according to claim 1, wherein $R^6$ is —$CONR^{11}R^{11}$, and $R^7$ is —$CONR^9R^{11}$, wherein each $R^{11}$ independently of any other $R^{11}$ is H or an unsubstituted $C_1$-$C_4$ alkyl, and
$R^9$ has the same meaning as defined above.

8. The compound according to claim 1, wherein $R^6$ and $R^7$ are —$CONR^9R^{11}$, and wherein
$R^9$ is $R^{11}$—$(Y$—$R^{10})_n$,
Y is selected from —$CONR^{11}$—, —$NR^{11}CO$—, —$NR^{11}COO$—, and —$NR^{11}CONR^{11}$—,
n is 1 or 2,
$R^{10}$ is an unsubstituted or monosubstituted $C_1$—, $C_2$—, $C_3$— or $C_4$ alkyl, and
$R^{11}$ is an unsubstituted $C_1$—, $C_2$—, $C_3$— or $C_4$ alkyl.

9. The compound according to claim 1, wherein $R^6$ is —$CONR^{11}{}_2$ and $R^7$ is —$CONR^9R^{11}$, wherein
$R^9$ is $R^{11}$—$(Y$—$R^{10})_n$,
Y is selected from —$CONR^{11}$—, —$NR^{11}CO$—, —$NR^{11}COO$—, and —$NR^{11}CONR^{11}$—,
n is 1 or 2,
$R^{10}$ is an unsubstituted or monosubstituted $C_1$—, $C_2$—, $C_3$— or $C_4$ alkyl, and
$R^{11}$ is an unsubstituted $C_1$—, $C_2$—, $C_3$— or $C_4$ alkyl.

10. The compound according to claim 1, wherein $R^6$ is H and $R^7$ is —$CONR^9R^{11}$, wherein
$R^9$ is $R^{11}$—$(Y$—$R^{10})_n$,
Y is selected from —$CONR^{11}$—, —$NR^{11}CO$—, —$NR^{11}COO$—, and —$NR^{11}CONR^{11}$—,
n is 1 or 2,
$R^{10}$ is an unsubstituted or monosubstituted $C_1$—, $C_2$—, $C_3$— or $C_4$ alkyl, and
$R^{11}$ is an unsubstituted $C_1$—, $C_2$—, $C_3$— or $C_4$ alkyl.

11. The compound of claim 1, wherein $R^7$ is —$CONR^9R^{11}$, wherein
$R^9$ is $(CH_2)_4$—$(Y$—$R^{10})_n$,
Y is selected from —$CONR^{11}$—, —$NR^{11}CO$—, —$NR^{11}COO$—, and —$NR^{11}CONR^{11}$—,
n is 1 or 2,
$R^{10}$ is an unsubstituted or monosubstituted $C_1$—, $C_2$—, $C_3$— or $C_4$ alkyl,
$R^{11}$ is an unsubstituted methyl or ethyl.

12. A compound selected from the following formulae:
N2,N2,N3,N3-tetraethyl-6,7-dihydroxy-5-nitro-naphthalene-2,3-dicarboxamide (A1),
(3-[[3-(diethylcarbamoyl)-6,7-dihydroxy-5-nitro-naphthalene-2-carbonyl]-ethyl-amino]propyl acetate) (A2),
N2-(6-aminohexyl)-N2,N3,N3-triethyl-6,7-dihydroxy-5-nitro-naphthalene-2,3-dicarboxamide (A4),
N2,N3,N3-triethyl-6,7-dihydroxy-N2-[4-[methyl(pentanoyl)amino]butyl]-5-nitro-naphthalene-2,3-dicarboxamide (A5),
tert-butyl N-[6-[[3-(diethylcarbamoyl)-6,7-dihydroxy-5-nitro-naphthalene-2-carbonyl]-ethyl-amino]hexyl]carbamate (A6),
4-[4-[[3-(diethylcarbamoyl)-6,7-dihydroxy-5-nitro-naphthalene-2-carbonyl]-ethyl-amino]butyl-methyl-amino]-4-oxo-butanoic acid (A8),
N2-[4-[4-aminobutanoyl(methyl)amino]butyl]-N2,N3,N3-triethyl-6,7-dihydroxy-5-nitro-naphthalene-2,3-dicarboxamide (A9),
tert-butyl N-[4-[4-[[3-(diethylcarbamoyl)-6,7-dihydroxy-5-nitro-naphthalene-2-carbonyl]-ethyl-amino]butyl-methyl-amino]-4-oxo-butyl]carbamate (A10),
N2,N3,N3-triethyl-6,7-dihydroxy-N2-[4-[[6-(2-methoxyphenyl)-6-oxo-hexanoyl]-methyl-amino]butyl]-5-nitro-naphthalene-2,3-dicarboxamide (A11) and
tert-butyl N-[1-cyclohexyl-2-[4-[[3-(diethylcarbamoyl)-6,7-dihydroxy-5-nitro-naphthalene-2-carbonyl]-ethyl-amino]butyl-methyl-amino]-2-oxo-ethyl]carbamate (A13).

13. A method for treatment of a condition selected from the group consisting Parkinson's disease, Alzheimer's disease, multi-drug resistant tuberculosis and obesity, comprising administering to a subject in need thereof a compound according to claim 1, thereby treating the condition.

14. A pharmaceutical composition comprising the compound according to claim 1; wherein said composition is formulated for inhalation or oral administration.

15. The pharmaceutical composition of claim 14, wherein said composition is formulated as a tablet, capsule, lozenge, powder, solution, suspension, or syrup.

* * * * *